(12) United States Patent
Pauletti et al.

(10) Patent No.: US 6,982,091 B2
(45) Date of Patent: *Jan. 3, 2006

(54) VAGINAL DELIVERY OF CHEMOTHERAPEUTIC AGENTS AND INHIBITORS OF MEMBRANE EFFLUX SYSTEMS FOR CANCER THERAPY

(75) Inventors: Giovanni M. Pauletti, Loveland, OH (US); James H. Liu, Cincinnati, OH (US); Leslie Z. Benet, Belvedere, CA (US); Wolfgang A. Ritschel, Cincinnati, OH (US)

(73) Assignee: UMD, Inc., Cincinnati, OH (US)

( * ) Notice: Subject to any disclaimer, the term of this patent is extended or adjusted under 35 U.S.C. 154(b) by 489 days.

This patent is subject to a terminal disclaimer.

(21) Appl. No.: 10/226,667

(22) Filed: Aug. 21, 2002

(65) Prior Publication Data

US 2003/0049302 A1    Mar. 13, 2003

Related U.S. Application Data

(60) Provisional application No. 60/315,877, filed on Aug. 29, 2001.

(51) Int. Cl.
*A61F 6/06* (2006.01)
*A61F 13/02* (2006.01)
*A61K 9/50* (2006.01)

(52) U.S. Cl. ............... 424/430; 424/431; 424/433; 424/500; 424/501; 424/502

(58) Field of Classification Search ............... 424/430, 424/431, 433, 500, 501, 502
See application file for complete search history.

(56) References Cited

U.S. PATENT DOCUMENTS 6,572,874 B1 * 6/2003 Harrison et al. ............ 424/430

OTHER PUBLICATIONS

Michael M. Gottesmann and Ira Pastan, The Multidrug Transporter, a Double-edged Sword, *The Journal of Biological Chemistry*, 263/25:12163-12166, (Sep. 5, 1988).
Adam B. Shapiro and Victor Ling, Reconstitution of Drug Transport by Purified P-glycoprotein, *The Journal of Biological Chemistry*, 270/27:16167-16175, (Jun. 7, 1995).
Christopher F. Higgins, ABC Transporters: From Microorganisms to Man, *Annu. Rev. Cell Biol.*, 8:67-113.
A. H. Schinkel and P. Borst, Multidrug Resistance Medicated by P-glycoproteins, *Cancer Biology*, 2:213-226, (1991).
Mary Ellen Krecic-Shepard, PhD, et al., Gender-Specific Effects on Verapamil Pharmacokinetics and Pharmacodynamics in Humans, *J. Clin Pharmacol.*, 40:219-230, (2000).

* cited by examiner

*Primary Examiner*—Carlos A. Azpuru
(74) *Attorney, Agent, or Firm*—Hana Verny

(57) ABSTRACT

Devices, methods, and compositions for cancer therapy by administration of chemotherapeutic agents and/or inhibitors of membrane efflux systems to the vagina for topical and systemic tumor targets.

33 Claims, 5 Drawing Sheets

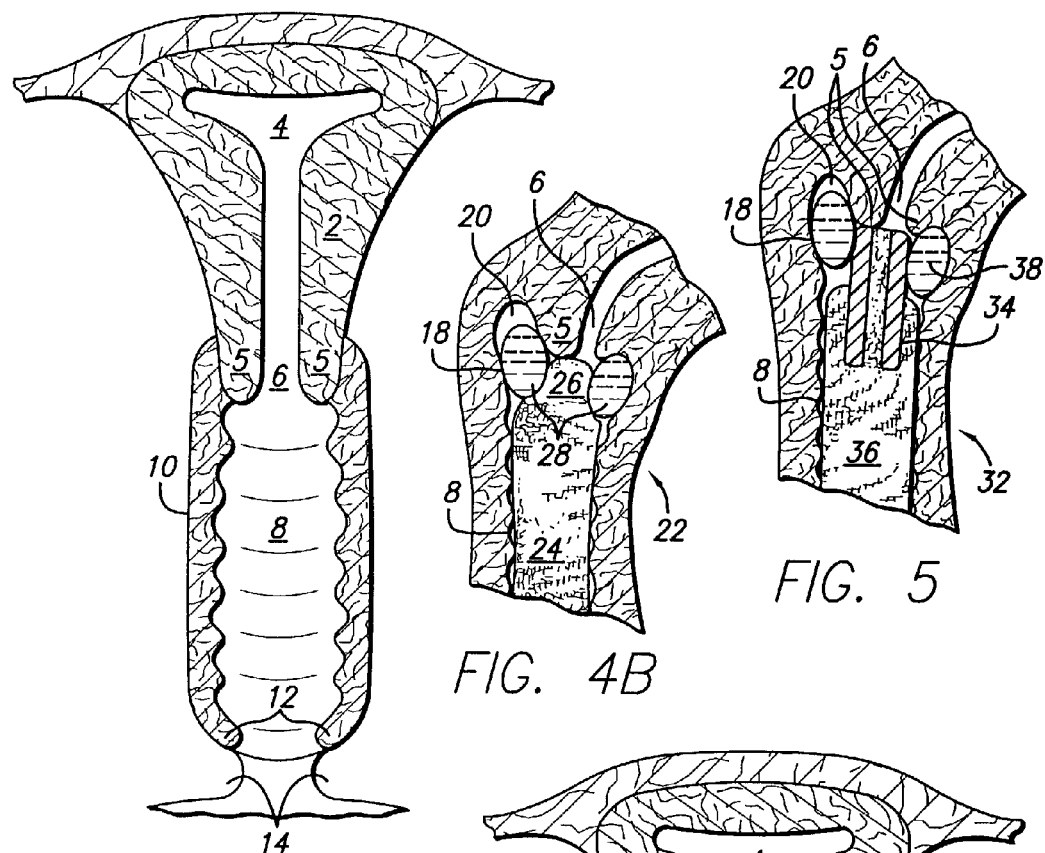
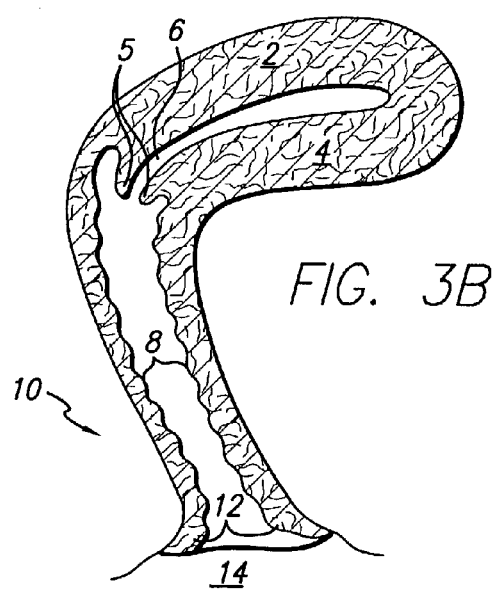
FIG. 3A
FIG. 3B
FIG. 4A
FIG. 4B
FIG. 5

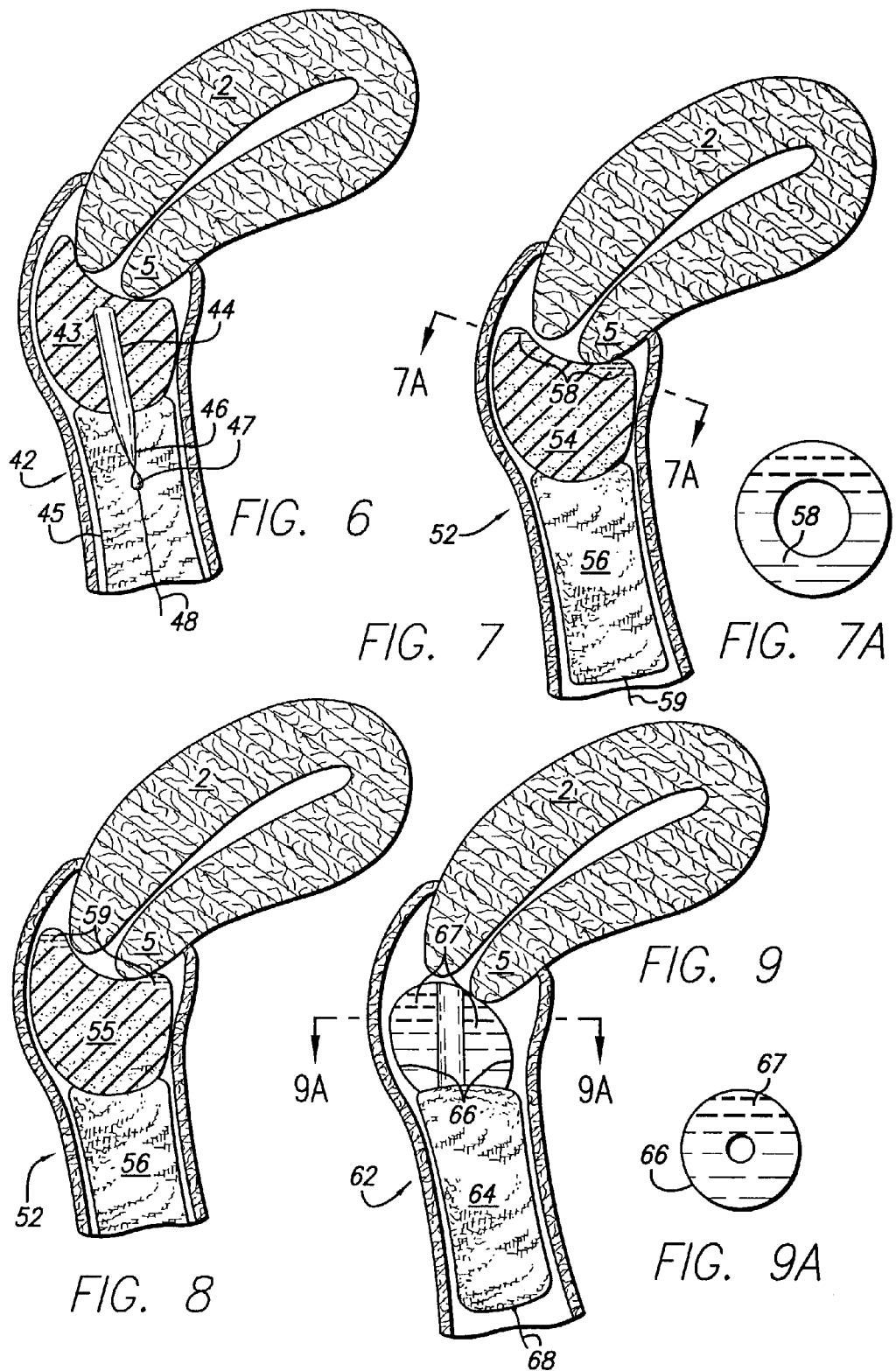

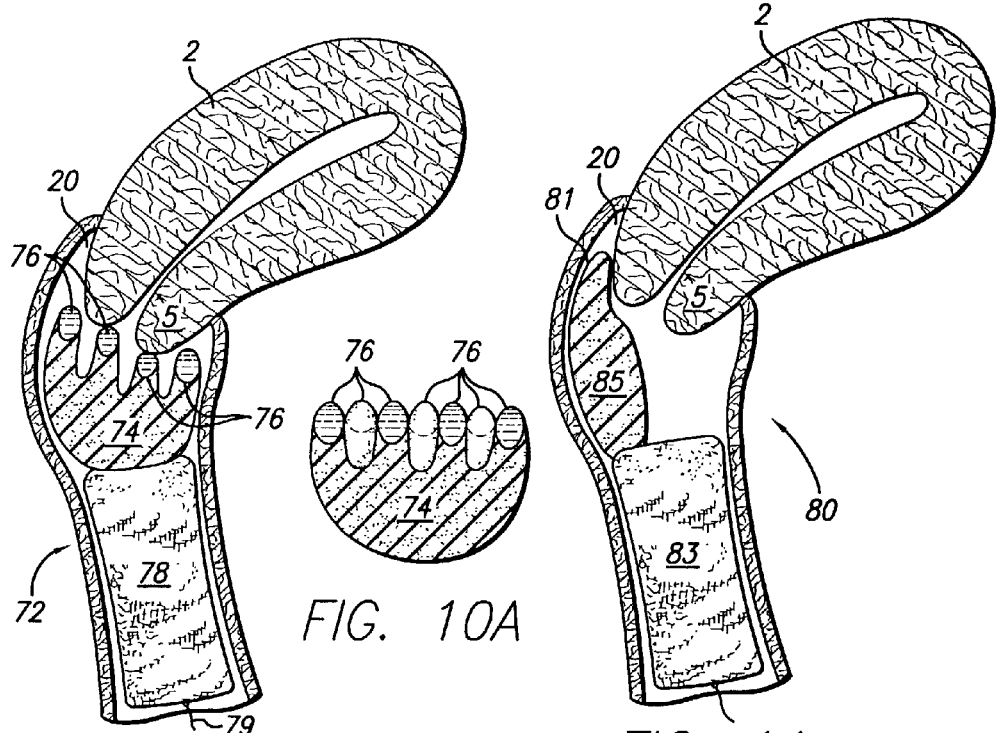
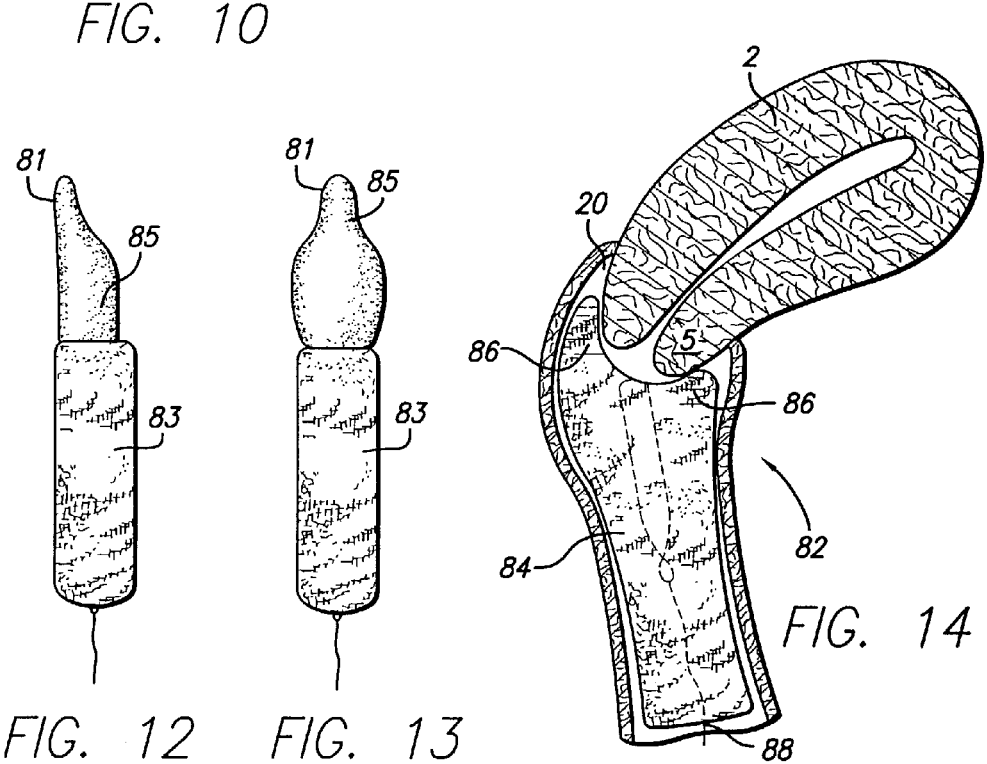

VAGINAL DELIVERY OF CHEMOTHERAPEUTIC AGENTS AND INHIBITORS OF MEMBRANE EFFLUX SYSTEMS FOR CANCER THERAPY

This invention is based on and claims priority of the Provisional application 60/315,877 filed on Aug. 29, 2001.

BACKGROUND OF THE INVENTION

1. Field of the Invention

The present invention concerns vaginal delivery of chemotherapeutic agents and/or inhibitors of membrane efflux systems for cancer therapy and a method for treatment of cancer. In particular, the invention concerns a method, composition and device for a mucosal and transmucosal delivery of a chemotherapeutic agent and/or inhibitor of membrane efflux systems to the vagina for topical vaginal and/or systemic cancer therapy using a mucoadhesive composition directly or incorporated into an intravaginal medicated device.

The composition of the invention or intravaginal device medicated with the mucosal composition of the invention delivers the chemotherapeutic agent and/or inhibitor of membrane efflux system into the vagina, provides a continuous contact with the vaginal mucosa, releases the agent from the formulation and delivers it transmucosally into the systemic circulation. The composition permits delivery of the therapeutic agent transmucosally through a vaginal wall to the systemic circulation or topically to the vaginal mucosa. The method avoids intravenous administration, permits extended continuous or pulsed delivery of the chemotherapeutic agents and/or inhibitors of membrane efflux systems and achieves delivery of higher concentrations of such agents to a site of neoplasias in the female.

The mucoadhesive composition comprises at least a therapeutic agent, a mucoadhesive agent, a sorption promoter and a carrier and optionally a penetration enhancer.

The mucoadhesive composition or medicated intravaginal device of the invention permits administration of lower concentrations of the drug than those needed for systemic administration, prevents leaking of the drug out of the vagina, results in greater systemic bioavailability than after oral administration and enhances transmucosal absorption of chemotherapeutic agents.

2. Background and Related Disclosures

Treatment of cancer or a cellular malignancy where there is a loss of normal control over cell growth, which results in unregulated growth, lack of differentiation and ability to invade local tissues and metastasize, poses a great challenge for the whole medical community. Because of the cancer's great aggressiveness, the available treatments, such as radiation and chemotherapy utilizing cytotoxic agents, are typically also very aggressive. As a result, the treatments of cancer result in many adverse reactions and toxicity.

Successful cancer therapy must be diverted to the primary tumors and to metastases, typically requiring a systemic, mainly intravenous, drug administration. Because of their aggressivity and toxicity, such intravenous administration often leads to phlebitis or collapse of the veins. Moreover, for intravenous injections it requires delivery of the treatment in the hospital or doctor's office as well as periods of following observation. To date, alternative treatments which would enable home administration of these drugs are limited.

Thus, it would be advantageous to have available alternative routes of administration of the chemotherapeutic agents and/or inhibitors of membrane efflux systems which would permit self-administration or, through extension, ongoing monitoring.

It has been estimated that in the United States half of the one million new cancer cases annually will be treated with systemic chemotherapy. Although the oral route would be the most preferred from a patient's perspective, absorption from the gastrointestinal tract is generally low due to various protein systems expressed in the intestinal mucosa. This includes metabolically active enzymes, such as cytochrome P450 superfamily, that degrade the therapeutic agent before it can reach the systemic distribution system. In addition, the intestinal mucosa contains a high level of specialized transport proteins that remove structurally unrelated drug molecules before reaching the systemic circulation. Examples of such membrane efflux systems that belong to the ABC transporter superfamily are P-glycoprotein (P-gp) and multidrug-resistance associated protein (MRP). It is also known that drug metabolizing enzymes and membrane efflux systems in the gastrointestinal mucosa act in concert, which results in low oral bioavailability of drugs that are substrates for both systems.

Biochemically, efflux systems in the gastrointestinal tract are related to the proteins that cause failure of chemotherapy in cancer patients as a result of multidrug resistance (MDR), as described in Ann. Rev. Cell Biol., 8:67 (1992). It is well documented that overexpression of membrane efflux systems such as P-gp and MRP in tumor cells confer MDR by actively decreasing net intracellular accumulation of diverse cytotoxic drugs (J. Biol. Chem., 263:12163 (1998); PNAS (USA), 85:3680 (1988); Semin. Cancer Biol., 2:213 (1991); and J. Biol. Chem., 270:16167 (1995)).

A new treatment of drug-resistant tumor cells includes administration of inhibitors of membrane efflux systems. The treatment with these inhibitors significantly increase accumulation of chemotherapeutic agents in drug-resistant tumor cells and, hence, provide a more effective tumor therapy at lower doses of the chemotherapeutic agents. However, since P-gp and MRP are also expressed in the gastrointestinal mucosa, where they serve as an important physiological defense barrier to environmental toxins, oral administration of inhibitors of membrane efflux systems may have only limited efficacy and also cause severe toxic side effects. As a consequence, administration of inhibitors of membrane efflux systems in cancer therapy is currently limited to the parenteral route using injections or short-term infusions.

Thus, it would be advantageous to have available alternative treatment which would overcome these intestinal membrane efflux systems and provide a continuous and predictable delivery of the chemotherapeutic drugs and/or inhibitors of membrane efflux systems to the tumor. To lessen toxicity of these drugs, such delivery should be preferably via absorption through other mucosal tissues than alimentary tract and should deliver the drug transmucosally to the general blood circulation to avoid a necessity to administer the drug intravenously.

Transvaginal delivery systems according to the invention could thus offer an alternative effective means of delivering therapeutic quantities of chemotherapeutic drugs for the treatment of neoplastic growth in the female because, in contrast to the gastrointestinal mucosa, the expression level of membrane efflux systems in the vaginal mucosa is significantly reduced.

Transvaginal delivery of anti-inflammatory and other drugs via a vaginal device has been discovered by inventors and is disclosed in the U.S. Pat. Nos. 6,086,909, 6,197,327 and 6,416,779 B1, incorporated herein by reference.

It is therefore a primary objective of this invention to provide a device, composition and a method for administration of chemotherapeutic agents and/or inhibitors of membrane efflux systems by transmucosal or topical vaginal delivery. The method of the invention provides a novel route of delivery of chemotherapeutic agents for treatment, control or maintenance of cancer which eliminates the need for parenteral administration, permits extended continuous or pulsed delivery of the drug to the vaginal mucosa locally and topically and transvaginal delivery of the drug to the general circulation. Additionally, the vaginal delivery of inhibitors of membrane efflux systems reduces the risk of toxic side effects following administration to cancer patients diagnosed with drug-resistant tumors. The method for treatment, control and maintenance of cancer comprises administering the chemotherapeutic agents and inhibitors of membrane efflux system intravaginally to the mucosa or transmucosally to the systemic circulation.

All references, patents and patent applications cited herein are hereby incorporated by reference in their entirety.

SUMMARY OF THE INVENTION

One aspect of the present invention is a method, composition and a device for vaginal delivery of effective doses of a chemotherapeutic agent and/or inhibitor of membrane efflux systems to the vaginal mucosa or transmucosally to the general blood circulation.

Another aspect of this invention is a method for treatment, management and control of cancer, said method comprising steps of contacting vaginal mucosa with a mucoadhesive composition or with an intravaginal device incorporated with said mucoadhesive composition comprising an antineoplastic agent selected from the group consisting of antiestrogens, androgen inhibitors, antibiotic derivatives, antimetabolites, cytotoxic agents, hormones, nitrogen mustard derivatives and steroids, each alone or in combination with an inhibitor of membrane efflux systems or further in combination with other pharmaceutical agents or pharmaceutically acceptable excipients and maintaining said composition or device in contact with said vaginal mucosa for a period of time permitting a continuous or pulsed delivery of the agent to or through vaginal mucosa, said composition further comprising at least a mucoadhesive agent, carrier and sorption promoter.

Still another aspect of this invention is a method for treating a human female suffering from cancer, said method comprising steps of contacting vaginal mucosa with a mucoadhesive composition or with an intravaginal device incorporated with said composition, the mucoadhesive composition comprising a chemotherapeutic agent and/or inhibitor of membrane efflux systems selected from but not limited to the group of compounds consisting of daunorubicin, doxorubicin, idarubicin, amrubicin, pirarubicin, epirubicin, mitoxantrone, etoposide, teniposide, vinblastine, vincristine, mitomycin C, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, and XR9576, alone or in combination with another pharmaceutical agent or a pharmaceutically acceptable excipient, said composition further comprising at least a mucoadhesive agent, a lipophilic or hydrophilic carrier and a sorption promoter.

Still another aspect of this invention is a mucosal composition comprising a chemotherapeutic agent and/or inhibitor of membrane efflux systems alone or in admixture with another pharmaceutical agent or a pharmaceutically acceptable excipient, said composition suitable for administration to the vagina or for incorporation into an intravaginal device for the vaginal or transmucosal vaginal delivery of the drug through the vaginal mucosa into the general circulation, said agent present in an amount sufficient to assert its therapeutic effect.

Still yet another aspect of this invention is a mucoadhesive composition comprising, in dosage unit form, from 0.001 to 3000 mg, preferably from 1 to 1000 mg, of a chemotherapeutic agent selected from the group consisting of but not limited to the group of daunorubicin, doxorubicin, idarubicin, amrubicin, pirarubicin, epirubicin, mitoxantrone, etoposide, teniposide, vinblastine, vincristine, mitomycin C, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, and XR9576, alone or in combination, or in combination with other pharmaceutical agents or pharmaceutically acceptable excipients suitable for intravaginal or transvaginal delivery of said agent to a human female, said composition consisting essentially of a combination of an effective amount of said chemotherapeutic agent and/or inhibitor of membrane efflux systems with at least a mucoadhesive agent promoting adhesion of the composition to the vaginal mucosa for delivery of the drug to the vaginal mucosa or with at least a mucoadhesive agent, a sorption promoter and a lipophilic or hydrophilic carrier for transmucosal delivery of the agent through the vaginal mucosa to the systemic circulation.

Yet another aspect of this invention is an intravaginal composition for vaginal or transmucosal vaginal delivery of a chemotherapeutic agent and/or inhibitor of membrane efflux systems, said composition administered directly or incorporated into a device selected from the group consisting of an intravaginal tampon, intravaginal ring, intravaginal pessary, intravaginal sponge, intravaginal tablet or intravaginal strip incorporated with a composition comprising a chemotherapeutic agent and/or inhibitor of membrane efflux systems from the group consisting of antiestrogens, androgen inhibitors, antibiotic derivatives, antimetabolites, cytotoxic agents, hormones, nitrogen mustard derivatives and steroids, formulated as a cream, lotion, foam, ointment, suppository, liposomal suspension, microemulsion, bioadhesive microparticle, bioadhesive nanoparticle, solution or gel.

Another aspect of this invention is a medicated device incorporated with a mucosal composition comprising at least a chemotherapeutic agent and/or inhibitor of membrane efflux systems in combination with a mucoadhesive agent, a sorption promoter and a lipophilic or hydrophilic carrier, suitable for treatment, management and control of cancer.

Yet another aspect of this invention is an intravaginal device for vaginal or transmucosal vaginal delivery of a chemotherapeutic agent and/or inhibitor of membrane efflux systems, said device selected from the group consisting of an intravaginal tampon, intravaginal ring, intravaginal pessary, intravaginal sponge, intravaginal tablet or intravaginal strip incorporated with a composition comprising a chemotherapeutic agent and/or inhibitor of membrane efflux systems from the group consisting of antiestrogens, androgen inhibitors, antibiotic derivatives, antimetabolites, cytotoxic agents, hormones, nitrogen mustard derivatives and steroids, formulated as a cream, lotion, foam, ointment, suppository, liposomal suspension, microemulsion, bioadhesive microparticle, bioadhesive nanoparticle, capsule, capsule containing microparticles, solution or gel, incorporated within said device.

Still yet another aspect of this invention is a medicated intravaginal device incorporated with a mucosal composition comprising, in dosage unit form, a chemotherapeutic agent selected from the group consisting of but not limited to the group of daunorubicin, doxorubicin, idarubicin, amrubicin, pirarubicin, epirubicin, mitoxantrone, etoposide, teniposide, vinblastine, vincristine, mitomycin C, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, and XR9576, alone or in combination, or in combination with other pharmaceutical agents or pharmaceutically acceptable excipients for intravaginal or transvaginal delivery to a human female, said composition consisting essentially of a combination of an effective amount of said chemotherapeutic agent and/or inhibitor of membrane efflux systems with at least a mucoadhesive agent promoting adhesion of the composition to the vaginal mucosa for delivery of the drug to the vaginal mucosa or with a mucoadhesive agent, sorption promoter and a lipophilic or hydrophilic carrier for transmucosal delivery of the agent through the vaginal mucosa to the systemic circulation.

BRIEF DESCRIPTION OF THE DRAWINGS

FIG. 3 is a representation of the female reproductive organs. FIG. 3A is cross-sectional representation of a portion of the female reproductive organs including the systemic circulation and vagina in the upright orientation. FIG. 3B is a cross-sectional side view representation of a portion of the female reproductive organs including the uterus and vagina.

FIG. 4 shows placement of a vaginal device of a drug delivery system according to the present invention. FIG. 4A is a front view and FIG. 4B is a cross-sectional side view representation of the vaginal area adjacent the cervix showing placement of a tampon device incorporating an annular delivery composition.

FIG. 5 is the representation of FIG. 3B showing placement of a tampon device according to the present invention.

FIG. 6 is the representation of FIG. 3B showing placement of a tampon device incorporating a distal porous foam section.

FIG. 7 is the representation of FIG. 3B showing placement of a tampon device incorporating a distal porous foam cup. FIG. 7A is a cross-sectional view of the embodiment shown in FIG. 7, taken in the direction indicated by the arrows labeled 7A in FIG. 7.

FIG. 8 is an alternate arrangement to the one shown in FIG. 7 in which medication is contained in the entire porous foam cup.

FIG. 9 is the representation of FIG. 3B showing placement of a tampon device incorporating a distal suppository or gel capsule. FIG. 9A is a cross-sectional view of the embodiment shown in FIG. 9, taken in the direction indicated by the arrows labeled 9A in FIG. 9.

FIG. 10 is the representation of FIG. 3B showing placement of a tampon device incorporating a distal foam cup having "fingers." FIG. 10A is a side view of the distal porous foam cup.

FIG. 11 is the representation of FIG. 3B showing placement of a tampon device incorporating a scoop-shaped distal porous foam section.

FIG. 12 is a side view of the embodiment shown in FIG. 11.

FIG. 13 is a front view of the embodiment shown in FIG. 11.

FIG. 14 is the representation of FIG. 3B showing placement of a tampon-like device incorporating distal fibers containing concentrated medication.

DEFINITIONS

Figure 1:
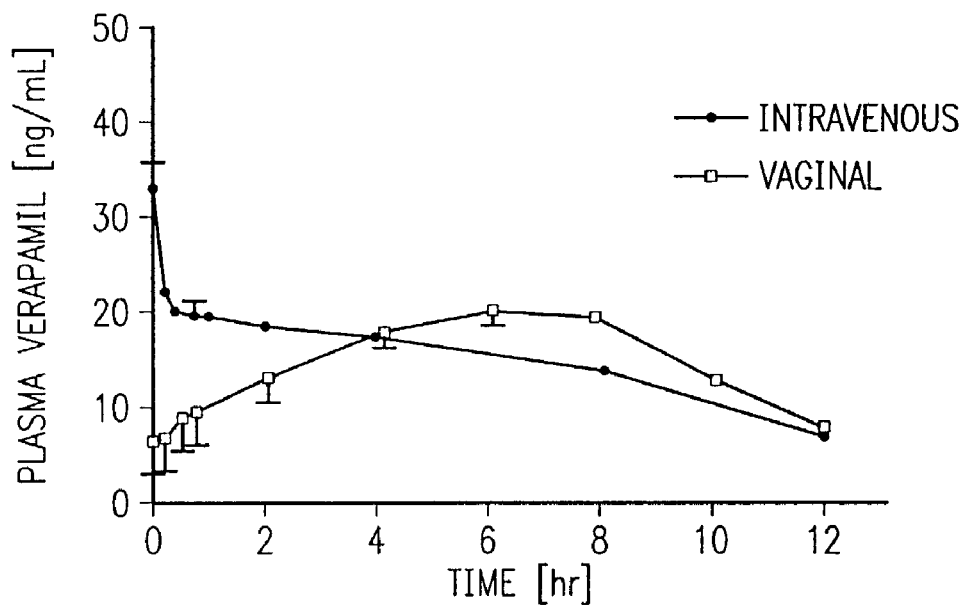
FIG. 1 is a graph showing concentration-time profiles of the P-glycoprotein substrate verapamil in plasma of white New Zealand rabbits following intravenous and vaginal administration of a single dose of the drug.

As used herein:

"Anti-cancer agent" means a chemotherapeutic agent or an inhibitor of membrane efflux systems P-glycoprotein and MRP.

"Drug" or "agent" means a therapeutically effective compound suitable for treatment, management or control of cancer or another condition.

"Pharmaceutical agent" or "therapeutical agent" means a chemotherapeutic agent, an inhibitor of membrane efflux system, a mixture of both, or any other pharmaceutically acceptable and therapeutically active agent.

"Chemotherapeutic" means an agent involved in treatment of disease, typically malignancy, by means of chemical substance or drug that exhibits cytostatic and/or cytotoxic effects on tumor cells.

"Inhibitor of membrane efflux systems" means a chemical compound, which is suitable to partially or completely block the functional activity of membrane efflux systems. Such inhibitor is typically a substrate for an enzyme, such as P-glycoprotein and MRP, involved in the efflux system.

"MRP" means multidrug-resistance associated protein.

"MDR" means multidrug resistance.

"Continuous delivery" means continuous and uninterrupted release of the drug from the formulation or device and delivering such drug in continuous manner.

"Pulsed delivery" means a release and delivery of the drug in intermittent intervals. Such pulsed delivery may be provided, for example, by formulating the drug in individual layers interspaced with inactive layer of dissolvable coatings or by using different formulating agents.

"Interstified stone oil" means a vegetable oil ethoxylated by replacing part of glycerol of the glycerides contained in vegetable oil by polyoxyethylene-glycols. Such replacement results in hydrophilic properties. Example of the interesterified stone oil is LABRAFIL®, particularly LABRAFIL® M 1944 CS, commercially available from Gattefosse.

"Mucosal" or "mucoadhesive" means a composition which is suitable for administration to the mucosal tissue and adhere to such mucosal tissue.

"Sorption promoter" means a compound which promotes penetration and permeation of tissue, that is getting into tissue as well as going through the tissue.

DETAILED DESCRIPTION OF THE INVENTION

This invention concerns a method, composition and a device for topical mucosal and transmucosal vaginal delivery of chemotherapeutic agents and inhibitors of membrane efflux systems for cancer therapy. The cancer therapy according to the invention is achieved by contacting vaginal mucosa with a mucosal composition or with a device incorporated with a mucosal composition comprising a chemotherapeutic agent or inhibitor of membrane efflux system or a combination thereof.

A device, composition and a method for administration of chemotherapeutic agents and/or inhibitors of membrane efflux systems are suitable for both the transmucosal delivery to the systemic circulation and a topical delivery to the vaginal mucosa.

The method of the invention provides a novel route of delivery of chemotherapeutic agents for treatment, control or maintenance of cancer which eliminates the need for parenteral administration, permits extended continuous or pulsed delivery of the drug to the vaginal mucosa locally and topically and transmucosal delivery of the drug to the general circulation. Additionally, the vaginal delivery of inhibitors of membrane efflux systems reduces the risk of toxic side effects following administration to cancer patients diagnosed with drug-resistant tumors.

I. Mucosal and Transmucosal Vaginal Delivery

A method for transmucosal and topical mucosal vaginal delivery comprises intravaginal administration of the mucoadhesive vaginal composition or the intravaginal device of the invention incorporated with such composition. The composition or the device delivers a chemotherapeutic agent and/or inhibitor of membrane efflux systems to and through the vaginal mucosa into the general circulation. Such delivery occurs without intravenous administration and thus eliminates serious adverse reactions typically connected with intravenously administered chemotherapeutic agents or inhibitors of membrane efflux systems.

A. Advantages of Vaginal Delivery

Existing systemic cancer therapy is almost exclusively limited to parenteral administration due to the barrier properties of the intestinal mucosa. Oral administration of chemotherapeutic agents prevents these agents to reach the systemic circulation in therapeutically relevant concentrations. Furthermore, oral administration of chemotherapeutic agents and inhibitors of membrane efflux systems, when attempted, often leads to significant gastrointestinal side effects such as acute nausea and vomiting, stomatitis, esophagitis, ulceration of stomach and colon, or increases risk of infections and/or toxic reactions as a result of reduced activity of membrane efflux systems in the alimentary and gastrointestinal mucosa. Extended or repeated parenteral administration of chemotherapeutic agents, as discussed above, has a potential to cause vascular collapse, vascular damage, phlebosclerosis, vascular hypersensitivities and other complications.

The vaginal route of delivery permits extended, continuous or pulsed delivery and administration of the drugs without need to visit the doctor's office or hospital. Using the mucosal composition and intravaginal device of the invention, the length of the drug delivery can be extended and the delivered dose may be lowered as the vaginal delivery by-passes the gastrointestinal tract and eliminates the intravenous administration with all its adverse effects and requirements.

The invention thus concerns discovery of an improved delivery of chemotherapeutic agents and inhibitors of the membrane efflux systems that overcomes the side effects and limitations observed during the parenteral and oral administration of chemotherapeutic agents and inhibitors of membrane efflux systems in the female by focusing the delivery of drug therapy directly to the vaginal mucosa and using a specifically formulated mucosal composition or an intravaginal device incorporated with such specifically formulated composition containing an appropriate amount of a therapeutical agent. Such composition promotes adhesion of the composition, including the drug released from the device, to the vaginal mucosa and further promotes a transmucosal delivery of the drug through vaginal mucosa to the general circulation.

The therapy according to the invention is suitable for treatment of all cancers via transmucosal delivery and also for treatment of ovarian, cervical or uterine cancers using a topical vaginal or transmucosal delivery, or both. Contacting the vaginal mucosa with chemotherapeutic drugs and/or inhibitors of membrane efflux systems incorporated into the composition according to this invention greatly increases concentrations of the drugs in the localized area of tumor and circumvents the gastrointestinal tract and intravenous delivery.

The newly developed vaginal delivery of the chemotherapeutic agents or inhibitors of membrane efflux system according to the invention thus represents an important improvement in the delivery of the chemotherapeutic agents and important advancement in cancer therapy.

B. Confirmation of Transmucosal Delivery

Mucosal or preferably transmucosal delivery according to the invention is suitable for delivery of chemotherapeutic agents as well as inhibitors of membrane efflux systems that belong to the ABC transporter superfamily. Examples of such inhibitors are P-glycoprotein (P-gp) and multidrug-resistance associated protein (MRP).

Biochemically, efflux systems in the gastrointestinal tract are related to the proteins that cause failure of chemotherapy in cancer patients as a result of multidrug resistance (MDR). Overexpression of membrane efflux systems such as P-gp and MRP in tumor cells result in multidrug resistance (MDR) by actively decreasing intracellular accumulation of cytotoxic drugs. Inhibitors of membrane efflux systems are therefore valuable anti-cancer agents that permit a significant increase in accumulation of chemotherapeutic agents in drug-resistant tumor cells. These inhibitors provide a more effective tumor therapy at lower doses of the chemotherapeutic agents.

To confirm that transmucosal delivery of the inhibitors, studies using verapamil, a membrane efflux system inhibitor for p-glycoprotein were performed. As discussed above, the p-glycoprotein is overexpressed in the gastrointestinal mucosa, however, its expression in the vaginal mucosa is significantly reduced. Consequently, transvaginal delivery systems of the invention, if experimentally confirmed, would prove to be an effective means of delivering therapeutic quantities of chemotherapeutic drugs for the treatment of neoplasms in the female.

The objective of this study was to determine whether vaginal delivery of verapamil leads to significantly improved bioavailability of verapamil. Studies were designed to compare bioavailability of verapamil administered orally, i.v., or transmucosally through vagina into systemic circulation.

Plasma pharmacokinetic of verapamil was determined in anesthetized female white New Zealand rabbits after intravenous and vaginal administration of verapamil at dose between 0.15–0.19 mg/kg. For analytical purpose, each dose was supplemented with a trace amount of [$^3$H] verapamil. Pharmacokinetic parameters were obtained by non-compartmental analysis using WinNonlin. Results are shown in FIGS. 1 and 2 and in Table 1.

Figure 2:
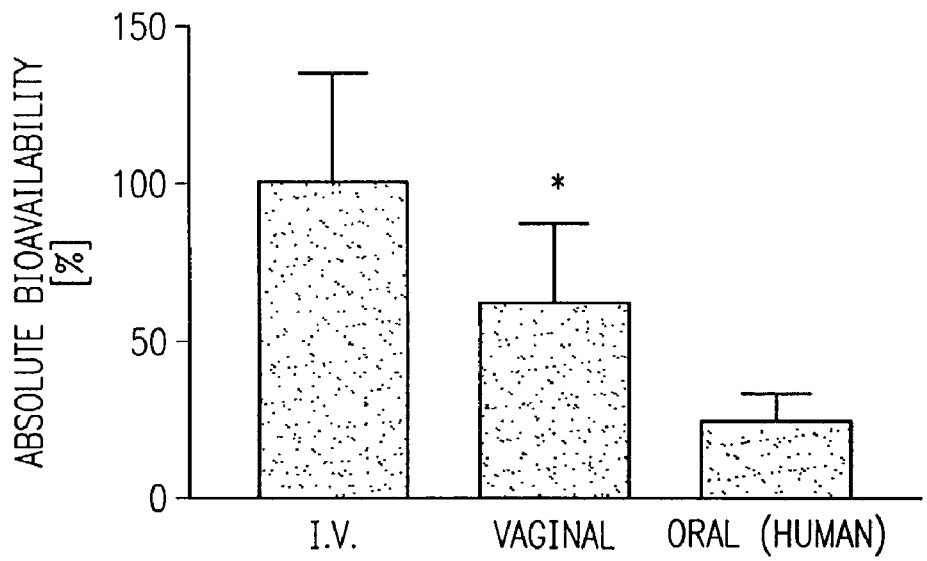
FIG. 2 is a graph illustrating absolute bioavailability of the P-glycoprotein substrate verapamil following intravenous and vaginal administration of the drug to the female white New Zealand rabbits.

FIG. 1 is a graph showing concentration-time profiles of the P-glycoprotein substrate verapamil in plasma of female white New Zealand rabbits following intravenous and vaginal administration of a single dose (0.15–0.19 mg/kg). Results are represented as mean±S.E.M (n=2–3).

Results seen in FIG. 1 show that following i.v. administration of a verapamil solution, verapamil rapidly disappeared from the vascular system, followed by a slower elimination phase with a mean terminal half-life of 9.5 hours. When delivered vaginally in form of a suppository formulated with 15% (w/w) of the sorption promoter transcutol, verapamil concentrations in plasma slowly increased to a maximum of 21.3±2.3 ng/ml measure after 5.5 hours.

Comparison of the dose-normalized areas under the curve (AUCs) for verapamil following vaginal and intravenous administration revealed an absolute bioavailability of 62.3±25.1%. Results are seen in FIG. 2.

FIG. 2 is a graph showing an absolute bioavailability of P-glycoprotein substrate verapamil following intravenous and vaginal administration to female white New Zealand rabbits (0.15–0.19 mg/kg, n=2–3). In comparison to the oral bioavailability of this drug in humans (*J. Clin.Pharmacol.*, 40: 219–230 (2000)), vaginal bioavailability in the rabbit model is significantly greater ($p<0.001$).

Table 1 lists individual pharmacokinetic parameters of verapamil following intravenous and vaginal administration in female white New Zealand rabbits.

TABLE 1

Pharmacokinetic Parameters of Verapamil Following Intravenous and Vaginal Administration in Female New Zealand Rabbits

| Parameter | Intravenous | Vaginal |
| --- | --- | --- |
| Dose [mg × kg$^{-1}$] | 0.15 | 0.15 – 0.19 |
| $c_{max}$ [ng × ml$^{-1}$] | 39.9 ± 4.9 | 21.3 ± 2.3 |
| $t_{max}$ [hr] | 0 | 5.5 ± 1.2 |
| AUC [ng × hr × mL$^{-1}$] | 1139.3 ± 408.1 | 709.9 ± 285.6 |
| $t_{1/2}$ [hr] | 9.5 ± 5.7 | 7.6 ± 1.2 |

Pharmacokinetic parameters were calculated from plasma verapamil drug concentration using the model-independent analysis module of WinNonlin.

The calculated terminal half-lives of verapamil, seen in Table 1, show that absorption across the vaginal mucosa after release of verapamil from the suppository is not rate-limiting.

The findings seen in FIGS. 1 and 2 and Table 1 confirm that verapamil, as a P-glycoprotein substrate, readily permeates the vaginal mucosal barrier. In contrast, oral absorption of verapamil is significantly reduced as demonstrated by a low oral bioavailability of 20–25%. These results show that vaginal delivery of substrates for membrane efflux systems, such as P-glycoprotein, increases the systemically available fraction of these therapeutic agents when compared to oral administration. Consequently, vaginal delivery of substrates for membrane efflux systems improves the therapeutic benefit of drugs used in the treatment of cancer.

C. Method for Delivery of the Cancer Therapy

A method of the invention is developed and particularly suitable for non-parenteral delivery of effective doses of a chemotherapeutic agent and/or inhibitor of membrane efflux systems topically to the vaginal mucosa or transmucosally to the general blood circulation.

The method, useful for treatment, management and control of cancer, comprises steps of contacting vaginal mucosa with a mucoadhesive composition or with an intravaginal device incorporated with such composition. Said composition comprises at least one chemotherapeutic agent or one inhibitor of membrane efflux systems selected from the group consisting of antiestrogens, androgen inhibitors, antibiotic derivatives, antimetabolites, cytotoxic agents, hormones, nitrogen mustard derivatives and steroids, alone, in combination with another chemotherapeutic agent or said inhibitor of membrane efflux systems, or in combination with another pharmaceutical agent or a pharmaceutically acceptable excipient, and maintaining said composition or device in contact with said vaginal mucosa for a period of time permitting a continuous or pulsed delivery of the agent to or through vaginal mucosa and necessary to deliver a therapeutic amount of the chemotherapeutic agent. Such time is typically one to several hours.

The delivery route utilizes the transmucosal composition directly or incorporated into an intravaginal device for transmucosal delivery and comprises delivery of a combination of the chemotherapeutic drug and/or inhibitors of membrane efflux systems with mucoadhesive agents, solubilizing agents, carriers and, optionally, penetration enhancing agents and solubilizers for transvaginal delivery.

Additionally, more than one drug may be present in the composition and the combination of a chemotherapeutic or any other pharmacologically active drug in tumor therapy, including inhibitors of membrane efflux systems, is intended to be within the scope of the invention.

The method thus includes a delivery of anti-cancer drugs in a combination with drugs which may enhance immune system, fight bacterial or viral infections, have analgesic effect and such other therapeutically and/or pharmaceutically active agents.

Specifically, the anti-cancer compounds suitable for delivery according to the method are selected from but are not limited to the group consisting of daunorubicin, doxorubicin, idarubicin, amrubicin, pirarubicin, epirubicin, mitoxantrone, etoposide, teniposide, vinblastine, vincristine, mitomycin C, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, and XR9576. Compounds may be administered alone or in combination with another pharmaceutical agent or a pharmaceutically acceptable excipient.

The method may be practiced either by administering the mucoadhesive composition directly to the vagina as a cream, lotion, foam, ointment, suppository, liposomal suspension, microemulsion, capsule, capsule containing microparticles, bioadhesive microparticle, bioadhesive nanoparticle, fluid or gel or by inserting the intravaginal device medicated with the above described mucosadhesive composition comprising a chemotherapeutic agent and/or inhibitor of membrane efflux systems incorporated therein. The device suitable for these purposes is selected from the group consisting of an intravaginal tampon, intravaginal ring, intravaginal pessary, intravaginal sponge, intravaginal tablet, intravaginal capsule, intravaginal cup and intravaginal strip.

Cancer therapy according to the invention comprises contacting the vaginal mucosa directly with a composition of the invention comprising the chemotherapeutic agent and/or inhibitor of membrane efflux systems. Such direct contact permits an immediate, extended continuous or pulsed delivery and efficacious treatment. Such direct treatment also permits use of only such a dosage of the chemotherapeutic agent and/or inhibitor of membrane efflux system as is therapeutically required for topical and/or systemic treatment of the affected tissue.

The method of the invention, suitable for cancer therapy, comprises providing a specifically formulated mucosal composition comprising the chemotherapeutic agent and/or inhibitor of membrane efflux systems or an intravaginal device incorporated with said composition, inserting said composition or device into the vagina and maintaining said composition or device in the vagina for a period of time required for a therapeutic effect of said mucosal composition. The composition is formulated to deliver the chemotherapeutic agent and/or inhibitor of membrane efflux systems to the target organ for treatment of cancer. For each of the treatments, the drug is formulated differently.

The method for cancer therapy using transmucosal delivery of the drug to systemic circulation involves adding to the composition of the invention components promoting absorption and/or transport and penetration of the drug through the vaginal mucosa. Such components are added in amounts sufficient to facilitate transmucosal delivery to the general circulation.

Transmucosal treatment is based on the concept that the upper vagina and the uterus have specific blood flow characteristics, either by a portal type circulation or by venous and lymphatic channels, permitting preferential transport and delivery of the pharmacological agents from the vagina directly to the blood circulation thereby by-passing the gastrointestinal tract absorption and liver detoxification.

The most specific demonstration of the transvaginal concept has been achieved by inventors with several types of drugs, as described in U.S. Pat. Nos. 6,086,909, and 6,197,327 and 6,416,779 B1, incorporated by reference. Chemotherapeutic agents or inhibitors of membrane efflux systems, when properly formulated, are transported through the vaginal wall in the same manner as described in the above patents.

The composition is a stand alone treatment or it is incorporated into a suitable intravaginal delivery device which assures the contact with the vaginal mucosa.

The composition or the medicated device according to the method is applied, that is, inserted intravaginally for from about ten minutes, preferably half an hour, to several hours once, twice or several times a day or week, as needed, or according to a treatment regimen. The device is typically provided in dry or wet form or may be wetted prior to insertion.

The method of the invention, as described herein and confirmed experimentally, provides several advantages over oral or intravenous administration of chemotherapeutic drugs and/or inhibitors of membrane efflux systems.

First, there is a continuous concentration of drug delivered to the vaginal mucosa and to the blood. This provides for higher bioavailability of the drug. Second, there is prevention of first-pass elimination of the drug in the intestinal mucosa and the liver by avoiding the gastrointestinal system. Third, the device of the invention provides a continuous drug depot which allows continuous and uninterrupted delivery of drug to the vaginal mucosa over a long period of time. Fourth, and very important, is the reduction of side effects due to avoidance of repeated intravenous administration of the drug or inhibition of gastrointestinal efflux systems that act as crucial physiological barriers to protect the interior milieu of the body from environmental toxins.

II. Mucoadhesive Compositions

A mucoadhesive composition of the invention for transmucosal delivery consists typically of four essential components. These components are a therapeutically active agent, a mucoadhesive agent, a lipophhilic or hydrophillic carrier and a sorption promoter. For topical delivery to the vaginal mucosa, the composition consists at least of two components, a therapeutically active agent and a mucoadhesive agent. The therapeutically active agents is either a chemotherapeutic agent and/or inhibitor of membrane efflux systems. These agents are formulated either alone or in admixture with another pharmaceutical agent or a pharmaceutically acceptable excipient. All the above mentioned components of the composition must be suitable for administration to the vagina or for incorporation into an intravaginal device for the vaginal or transmucosal vaginal delivery of the drug through the vaginal mucosa into the general circulation. The therapeutically active compound is present in an amount sufficient to assert its therapeutic effect, typically from about 0.001 to about 3000 mg, preferably from 1 to 1000 mg, most preferably from 100 to about 500 mg.

The mucoadhesive composition is typically formulated in dosage unit form, and contains a chemotherapeutic agent or an inhibitor of membrane efflux systems selected generally from antiestrogens, androgen inhibitors, antibiotic derivatives, antimetabolites, cytotoxic agents, hormones, nitrogen mustard derivatives and steroids, alone, in combination, or in combination with other pharmaceutical agents or pharmaceutically acceptable component and excipients for intravaginal or transvaginal delivery to a human female.

The composition typically contains from 0.001 to about 3000 mg, preferably from 1 to 1000 mg, of a chemotherapeutic agent and/or inhibitor of membrane efflux systems with at least a 5–25% of mucoadhesive agent promoting adhesion of the composition to the vaginal mucosa, from about 5 to about 25% of sorption promoter assuring the penetration of the drug through the mucosa and from about 40 to about 95% of a lipophilic or hydrophilic carrier serving as a vehicle for the drug, and optionally, from about 0 to about 30%, preferably about 1 to 5% of a permeation enhancer or solubilizer for transmucosal delivery of the agent through the vaginal mucosa to the systemic circulation.

Specific therapeutical anti-cancer drug suitable for delivery according to this invention using the above composition are daunorubicin, doxorubicin, idarubicin, amrubicin, pirarubicin, epirubicin, mitoxantrone, etoposide, teniposide, vinblastine, vincristine, mitomycin C, paclitaxel, docetaxel, actinomycin D, colchicine, topotecan, irinotecan, gemcitabine, cyclosporin, verapamil, valspodor, probenecid, MK571, GF120918, LY335979, biricodar, terfenadine, quinidine, pervilleine A, and XR9576, alone, or in combination.

The composition is formulated as a cream, lotion, foam, ointment, suppository, liposomal suspension, microemulsion, bioadhesive microparticle, bioadhesive nanoparticle, capsule, capsule containing microparticles, solution or gel, and can be delivered as stand alone or incorporated within an intravaginal device.

Alternatively, the composition can be incorporated into an intravaginal device or a coating of such device, for example, a tampon or tampon-like device coating, or incorporated into a sponge, foam, strip, pessary, or other material. Absorbent material or matrix of such devices may be impregnated with a drug containing liquid solution, suspension lotion, cream, microemulsions or suspension of liposomes, bioadhesive nanoparticles, or bioadhesive microparticles. The devices of the invention are described in greater detail below in section III.

Any form of drug delivery system which will effectively deliver the anti-cancer agent to the vaginal mucosa or transmucosally through the vaginal mucosa into the systemic circulation is intended to be included within the scope of this invention.

A. Anti-cancer Therapeutical Agents

The anti-cancer therapeutical agents are chemotherapeutic agents or inhibitors of membrane efflux system generally selected from the following groups and types of compounds: antiestrogens, androgen inhibitors, antibiotic derivatives, antimetabolites, cytotoxic agents, hormones, nitrogen mustard derivatives or steroids.

Specific chemotherapeutic compounds are selected from but not limited to the group of compounds including daunorubicin, doxorubicin, idarubicin, amrubicin, pirarubicin, epirubicin, mitoxantrone, etoposide, teniposide, vinblastine, vincristine, mitomycin C, paclitaxel, docetaxel, actinomycin D, colchicine, topotecan, irinotecan, gemcitabine and any other compound know now or which will become known in future to have similar chemotherapeutic properties. All these compounds are intended to be covered by this invention.

Specific inhibitors of membrane efflux system are generally compounds which are substrates and/or inhibitors for the membrane efflux systems, such as P-glycoprotein or MDR. The inhibitors a P-glycoprotein are selected from but not limited to the group of compounds represented by cyclosporin, verapamil, valspodor, biricodar, quinidine, terfenadine, pervilleine A, and investigational drugs currently known under their coded names GF120918, LY335979, OC144–093 (Ontogen) and XR9576. The MRP2 inhibitors are probenecid and the Merck investigational compound known under its coded name MK571. Any other compound know now or which will become known in future to have similar inhibitory properties is intended to be covered by this invention.

The compounds of the invention are administered in from about 0.001 to about 3000 mg/day, preferably in about 1 to about 1000 mg/day dosages. The individual chemotherapeutic agents and inhibitors are administered in different dosages and ranges depending on their activity. Exemplary dosage for colchicin are, for example in a range from about 4 to about 8 mg/day, paclitaxel from about 60 to about 100 mg/m$^2$, topotecan from about 0.5 to about 1.5 mg/m$^2$, doxorubicin from about 100 to about 1000 mg/day, vincristine about 1–2 mg/dose, verapamil from about 10 to about 125 mg/dose and cyclosporin in about 60 mg/dose.

The chemotherapeutic agents or inhibitors of membrane efflux systems are formulated in said composition alone, in admixture of two or more or in admixture of the chemotherapeutic agent and inhibitor and/or in combination with another pharmaceutical agent or a pharmaceutically acceptable component or excipient.

B. Pharmaceutical Compositions and Formulations

In order to achieve desirable drug release at a site where it can act either directly on the vaginal mucosa or to be transported transmucosally through the vaginal wall to the systemic circulation, the chemotherapeutic drug and/or inhibitor of membrane efflux systems is formulated in conjunction with other components which permit its adhesion to the vaginal mucosa and absorption through the vaginal mucosa to the systemic circulation. A resulting composition typically contains at least a mucoadhesive agent, a sorption promoter and a non-toxic lipophilic or hydrophilic carrier, and optionally, a permeation enhancer and/or a solubilizing agent and/or another pharmaceutically acceptable excipient suitable for vaginal delivery, such as a buffer, filler, stabilizer, emulsifier, and any such other excipient as is known in the art to be useful for these purposes.

Any component and/or excipient used in formulations of this invention needs to be approved for human use and acceptable for use in the vagina with understanding that not all excipients approved for oral use may be approved and/or suitable for vaginal use.

1. Individual Components

For vaginal transmucosal delivery, the formulation of the invention comprises the following components.

a. Anti-cancer Agent

The anti-cancer agent is selected from the drugs described above and is typically present in from about 0.01 to about 10%, by weight. The agent is typically either lipophilic or hydrophillic and, depending on its affinity, it requires different formulation protocol.

b. Mucoadhesive Agent

For vaginal transmucosal delivery, the composition comprises, as an essential component, a mucoadhesive agent. The mucoadhesive agent permits a close and extended contact of the composition, or the drug released from said composition, with mucosal surface by promoting adherence of said composition or drug to the mucosa. The mucoadhesive agent is preferably a polymeric compound, such as preferably, a cellulose derivative but it may be also a natural gum, alginate, pectin, or such similar polymer. The most preferred cellulose derivative is hydroxypropyl methylcellulose available under the trade name METHOCEL®, commercially available from Dow Chemical Co.

The mucoadhesive agent is present in from about 5 to about 25%, by weight, preferably in from about 10 to about 15% and most preferably about 10%.

c. Sorption Promoters

The mucoadhesive composition additionally includes a sorption promoter present in from about 2 to about 30%, by weight. Sorption promoter assures a permeation and penetration, that is moving through the tissue and entering systemic blood circulation of the drug through the vaginal mucosa. Sorption promoters include non-ionizable glycol ester derivatives, such as polyethylene glycol caprylic/capric glycerides known as LABRASOL® from Gattefossé, glycol derivatives with glycerol esters, such as oleic acid esters of propylene glycol and glycerol known as ARLACEL® 186 from Imperial Chemical Industries. Particularly preferred are non-ionizable glycol ether derivatives, such as, most preferably, ethoxydiglycol known under its trade name TRANSCUTOL® and commercially available from Gattefosse, or interesterified stone oil, for example LABRAFIL M 1944CS, commercially available from Gattefosse. The interesterified stone oil is a vegetable oil ethoxylated by replacing part of glycerol of the glycerides contained in vegetable oil by polyoxyethylene-glycols.

d. Lipophilic and Hydrophilic Carriers

Depending on the drug affinity, the composition of the invention additionally comprises either the lipophilic or the hydrophilic carrier that is appropriate for the pharmaceutical agent. Such carrier is typically present from about 30 to about 95%, by weight.

The carrier is selected from such compounds for which the drug has low affinity. Thus the lipophilic carrier is appropriate for formulation of the hydrophilic drug and the hydrophilic carrier is appropriate for formulation of the lipophilic drug.

i. Lipophilic Carriers

Preferred lipophilic carriers for use with hydrophilic drugs include any medium chain triglycerides and/or a saturated mono-, di- or triglyceride of fatty acids, particularly those having carbon chain of from 8 to 18 carbons, or a mixture thereof. Examples of the lipophilic carrier are saturated glycerides known and available under the trade name SUPPOCIRE® AS2 or CS2, and related compounds commercially available, for example, from Gattefosse, Westwood, N.J.

ii. Hydrophillic Carriers

Preferred hydrophilic carriers include polyethylene glycols of molecular weight between about 200 and 8000, OR derivatives or mixtures thereof, such as PEG 6000/PEG 1500, or PEG 6000/PEG 1500/PEG 400, or PEG 6000/PEG 400, or PEG 8000/PEG 1500, commercially available from, for example, Sigma/Aldrich, St. Louis, Mo.

e. Penetration Enhancers

Penetration enhancers are compounds which assist in improving penetration properties of the drug or their mixtures by changing the surface properties of the drugs or their mixtures, or drug containing solutions or suspensions. These compounds thus, in a way act as solubilizers. Examples of the penetration enhancers are non-ionic surfactants.

f. The Solubilizing Agents

The composition optionally includes also a solubilizing agent, such as complex-forming solubilizer citric acid, ethylenediamine-tetraacetate, sodium meta-phosphate, succinic acid, urea, cyclodextrin, polyvinylpyrrolidone, diethylammonium-ortho-benzoate, or micell-forming solubilizers such as tweens and spans, for example Tween 80. Other solubilizer useful for the compositions of this invention are polyoxyethylene sorbitan fatty acid ester, polyoxyethylene n-alkyl ethers, n-alkyl amine n-oxides, poloxamers, organic solvents, phospholipids and cyclodextrines.

f. Additional Excipients

The composition of the invention may additionally contain other excipients, such as, fillers, emulsifiers, stabilizers, buffers, and others as appropriate. Examples of these excipients are isostearylstearate, isopropyl myristate, glycerin, mineral oil, polycarbophil, carbomer 934P or 940, hydrogenated palm oil, glyceride, sodium hydroxide, sorbic acid, and purified water.

2. Preferred Formulations

All and every formulation which contains components of the invention in ranges given above are intended to be within the scope of this invention. Few compositions presented here as preferred formulation are only exemplary and are not intended to limit the scope of the invention in any way.

Preferred formulations for hydrophilic drugs comprise between about 0.01–10%, by weight, of the drug, about 60–90%, by weight, lipophilic carrier, between about 5–25%, by weight, mucoadhesive agent, between about 1–25%, by weight, sorption promoter and optionally a penetration enhancer or solubilizing agent, usually present in 1–30%, by weight.

Preferred formulations for the lipophilic drugs comprise between about 0.01–10%, by weight, of the drug, about 30–90%, by weight of hydrophilic carrier, between about 1–25%, by weight, of mucoadhesive agent, between 1 and 25% of sorption promoter and optionally between about 1–30%, by weight, solubilizing agent and/or permeation enhancer.

In another preferred embodiment of the invention, 0.01–10% of the drug is formulated with other components such as between about 60 to 90% by weight lipophilic carrier, between about 5 to 20% mucoadhesive agent, between about 10–20% of sorption promoter, between 0 to 30% solubilizing agent, and between about 1 to 30% permeation enhancer and.

In another preferred embodiment of the invention, 0.01–10% drug is formulated in admixture with about 60 to 90%, by weight, of hydrophilic carrier, between about 5 and about 20% of mucoadhesive agent, between about 10 and 15% of sorption promoter and optionally between 0–30% of solubilizing agent and/or between about 1 and 30% of permeation enhancer.

In another preferred embodiment of the invention, the drug is formulated as a vaginal suppository which includes 0.01–10% of a hydrophilic drug, 75% of a lipophilic carrier SUPPOCIRE® AS2, 2% hydroxypropyl methylcellulose, and 15% of ethoxydiglycol (TRANSCUTOL®). The suppository may be a stand-alone device or be incorporated into a tampon or tampon-like device.

In another preferred embodiment of the invention, the drug is formulated as a vaginal suppository which includes 0.01–10% of a lipophilic drug, 75% of a hydrophilic carrier PEG 6000/PEG 1500, 2% hydroxypropyl methylcellulose, and 15% of ethoxydiglycol (TRANSCUTOL®). The suppository may be a stand-alone device or be incorporated into a tampon or tampon-like device.

3. Process for Formulating Hydrophilic or Lipophilic Drugs

The lipophilic or hydrophilic chemotherapeutic agents or inhibitors of membrane efflux system are formulated using the following process.

In a general method for preparing a formulation for a hydrophilic drug, the lipophilic carrier is melted at 45–50° C. in a heated vessel. The mucoadhesive agent is added to the carrier with stirring. The preferred hydrophilic drug is dissolved in the sorption promoter combined with the penetration enhancer and solubilizing agent. This mixture is added to the carrier/mucoadhesive agent suspension. The final formulation is poured into molds of the desired size and shape or incorporated into a device of the invention. The molds which are stored in a refrigerator at 4–6° C.

In a general method for preparing a formulation including a lipophilic drug, the hydrophilic carrier is melted in a heated vessel at an appropriate temperature recommended by manufacturer. The mucoadhesive agent is added to the carrier with stirring. The preferred lipophilic drug is dissolved in the sorption promoter, and penetration enhancer combined with the solubilizing agent are optionally added. This mixture is admixed with the carrier/mucoadhesive agent suspension. The final formulation is poured into molds of the desired size and shape or incorporated into a device of the invention. The final formulation is then placed in a refrigerator at 4–6° C.

4. Sustained Release

In one embodiment, the composition can be formulated as a sustained and controlled release drug system.

The drug which is formulated for controlled and sustained release is formulated either for continuous release or for pulsed delivery.

Continuous release or delivery means continuous and uninterrupted release of the drug from the formulation or device wherein the drug is formulated either in the matrix, microparticle, bioadhesive particle, liposomal suspension or any another system typically used for such release.

Pulsed release or delivery is a delivery of the drug in intermittent intervals. Such pulsed delivery may be provided, for example, by formulating the drug in the matrix, microparticle, bioadhesive particle, liposomal suspension or any another system, as described for continuous delivery, in individual layers interspaced with inactive layer of inactive, for example, dissolvable coatings or by using different formulating agents. Methods and formulating agents for sustained delivery are known in the art.

The controlled release, a drug delivery system must be capable of controlled release of a drug into the vaginal mucosa over several hours or more. This is achieved by the addition of time release additives such as hydrogel-forming polymers, non-errodible matrices, etc., known in the art.

Additionally, during the menstrual cycle when the pH of the vagina changes, the drug delivery systems additionally may contain buffers to stabilize pH to enhance absorption.

The sustained release composition of the invention is typically in a form of a cream, lotion, foam, suppository, tablet, microparticle, nanoparticle, capsule containing microparticles, liposomal suspension fluid, bioadhesive systems and microemulsions.

5. Bioadhesive Systems and Microemulsions

Bioadhesive systems and microemulsions are formulations particularly suitable for vaginal transmucosal delivery.

The microemulsion may contain pharmaceutically acceptable surfactants, for example, LABRASOL®, PLUROL® isostearate (Gattefossé), co-solvents such as isopropanol or ethanol, and water. Microemulsions containing one or more of the above components have been shown to improve bioavailability of chemotherapeutic drugs.

Bioadhesive microparticles or bioadhesive nanoparticles constitute still another intravaginal drug delivery system suitable for use in the present invention.

The bioadhesive systems use derivatives of cellulose such as hydroxypropyl cellulose and polyacrylic acid. They release the cytotoxic or chemotherapeutic drugs for up to five days once they are placed in the appropriate formulation. This system represents a multi-phase liquid or semi-solid preparation which does not seep from the vagina as do most current suppository formulations. The microparticles or nanoparticles cling to the wall of the vagina and release the drug over a several hour period of time. Many of these systems were designed for nasal use, as described in U.S. Pat. Nos. 4,756,907, and 6,200,590 incorporated herein by reference, but can be easily modified for use in the vagina. The bioadhesive system may comprise microparticles or nanoparticles filled with the chemotherapeutic agent and/or inhibitor of membrane efflux systems and may contain a surfactant for enhancing solubility and/or uptake of the drug. The microparticles have a diameter of 1–100 μm, whereas nanoparticles have a diameter of 10–1000 nm. Microparticles and nanoparticles can be prepared from starch, gelatin, albumin, collagen, or dextran according to methods known in the art.

Bioadhesive tablets are another drug delivery system suitable for transmucosal delivery. These bioadhesive systems use hydroxypropyl cellulose and polyacrylic acid. They release drugs for up to five days once they are placed in the appropriate formulation. The tablet of the invention has the shape of a suppository or a tampon so that the maximum contact is achieved between the vaginal wall and the tablet surface or such a shape as is suitable for incorporation into the device.

Bioadhesive microparticles- or nanoparticles, described above, constitute still another drug delivery system suitable for use in the present invention. This system is a multi-phase liquid or semi-solid preparation which does not seep from the vagina as do most current suppository formulations. The substances cling to the wall of the vagina and release the drug over a several hour period of time or are released from the device.

The drug can also be incorporated into creams, lotions, foams, paste, ointments, microemulsions, liposomal suspensions, and gels which can be applied to the vagina using an applicator. Processes for preparing pharmaceuticals in these vehicles can be found throughout the literature.

Suitable nontoxic pharmaceutically acceptable excipients for use in the compositions of the present invention will be apparent to those skilled in the art of pharmaceutical formulations and examples are described in *REMINGTON: The Science and Practice of Pharmacy*, $20^{th}$ Edition, A. R. Gennaro, ed., (2000). The choice of suitable carriers will depend on the exact nature of the particular vaginal dosage form desired, e.g., whether the chemotherapeutic agent and/or inhibitor of membrane efflux systems is/are to be formulated into a cream, lotion, foam, ointment, paste, solution, microemulsions, liposomal suspension, microparticles, nanoparticles or gel, as well as on the physicochemical properties of the active ingredient(s).

Although the compositions described above typically contain only one pharmaceutically active ingredient from the group of chemotherapeutic agents or inhibitors of membrane efflux systems for treatment of cancer and neoplastic growth, such compositions may additionally contain other pharmaceutical agents or a combination thereof, such as, for example, pain killers, antivirals, antipruritics, corticosteroids and other agents which may enhance the therapeutic effect of the primary drug.

All bioadhesive systems described above may be administered directly or via an intravaginal device.

III. Device and/or System for Transvaginal Drug Delivery

The composition of the invention for transmucosal delivery is administered either directly to the vagina or is incorporated into the intravaginal device.

The intravaginal device of the invention is typically a tampon, tampon-like device, ring, pessary, strip, cup or foam which has a solid structure into which the formulation is incorporated and from which it is released in a timely fashion over a period of time. The time period is typically limited to from several minutes to 24 hours, preferably 4–8 hours, which is a hygienically acceptable time to leave the device in place.

Advantages of the medicated intravaginal device include continuous delivery of a predictable amount of the drug. The device may also have a washable and reusable design, such as, vaginal ring or pessary.

The intravaginal device for vaginal or transmucosal vaginal delivery of a chemotherapeutic agent and/or inhibitor of membrane efflux systems is an intravaginal tampon, intravaginal ring, intravaginal pessary, intravaginal sponge, intravaginal tablet or intravaginal strip incorporated with a composition comprising a chemotherapeutic agent and/or inhibitor of membrane efflux systems formulated as a cream, lotion, foam, ointment, suppository, liposomal suspension, microemulsion, bioadhesive microparticle, bioadhesive nanoparticle, solution or gel.

The device may be configured for controlled release of the chemotherapeutic drugs or inhibitors of membrane efflux system where the drug incorporated into the device is formulated as a sustained release system, as described above.

In one embodiment, the invention provides a tampon device for delivering a chemotherapeutic agent and/or inhibitor of membrane efflux systems across the vaginal mucosa comprising an absorbent vaginal tampon having a proximal end and a distal end. A cup-shaped porous foam portion at the distal end fits around the cervix of the systemic circulation and contains a pharmaceutical agent for delivery to the cervix. The device may also include a nonabsorbing axial tube having a distal opening and extending through the porous foam cup into the tampon for conducting blood flow to the absorbent material. Optionally, a retrieval string or tape connected to the tampon device is also included. The absorbent vaginal tampon contains any of the above-mentioned drugs or be coated with the drug and be used as a medicated tampon for individual drug or drug combination delivery.

In another embodiment of a tampon device, the distal porous foam cup has a rim which encircles the cervix. The rim has high concentrations of medication and is positioned away from the direct flow of blood which exudes from the cervix during menstruation.

In another embodiment of a tampon device, the distal porous foam cup has a rim which encircles the cervix. The rim has fingers extending into the fornix areas around the cervix and the tips of the fingers have high concentrations of medication and are positioned away from the direct flow of menstrual blood.

In another embodiment of a tampon device, a distal porous foam section is in the shape of a scoop, which only partially encircles the cervix. The porous foam scoop has a nib-like shape which is designed to wedge itself into the posterior fornix. The porous foam scoop is designed to deliver medication to the vaginal wall along the entire length of the porous foam scoop.

In another embodiment, a tampon device is sheathed in a thin, supple, non-porous material such as a plastic film or a coated gauze that surrounds the absorbent tampon material like a skirt and opens like an umbrella when it comes in contact with the vaginal environment. A drug incorporated into a strip, ideally suspended in a wax-like carrier that melts at body temperature, encircles the sheathed tampon. Contact with vaginal fluids or menstrual flow causes the tampon to swell, forcing the skirt to open like an umbrella and to press tightly against the vaginal wall, putting the drug in contact with the vaginal mucosa while effectively preventing the drug from being absorbed into the tampon.

In another embodiment of a tampon device, distal fibers of the tampon which contact the cervix have high concentrations of pharmaceutical agent for delivery of the agent to the cervical tissue.

In another embodiment of a tampon device, the tampon device has an outer tubing having perforations, the outer tubing is concentric around an axial tube. The device has a distal porous foam section which in its dehydrated state is tight around the outer tubing. A bladder is located proximally to the porous foam and filled with liquid pharmaceutical agent. The bladder is connected to the outer tubing. An outer sheath covers the tampon. The sheath has an annular constriction distal to the bladder such that deployment of the tampon through the distal end of the sheath causes the liquid in the bladder to be forced out distally through the perforated outer tubing and into the porous foam.

In another embodiment of a tampon device, the tampon device has an annular delivery composition around the distal end. The composition contacts the vaginal mucosa for delivery of the chemotherapeutic agent and/or inhibitor of membrane efflux systems. A non-absorbing axial tube opens distally and extends into the tampon for conducting blood flow to the absorbent material proximal to the porous foam. The annular composition can be a suppository, cream, ointment, foam, microparticles, paste, or gel.

Embodiments of the invention may include tampon devices of a standard length, or may be longer or shorter than standard tampons to facilitate positioning the tampon device closer to or in contact with the vaginal wall or with the cervix, depending on the location of tumor.

For purposes of simplifying the description of the invention and not by way of limitation, tampon or tampon-like devices, such as a suppository, for drug delivery will be described hereinafter, it being understood that all effective delivery systems are intended to be included within the scope of this invention.

Particular device embodiments of the invention are described in greater detail in FIGS. 3–17. FIGS. 3A and 3B show anatomical arrangement of the vagina, systemic circulation and other organs. FIGS. 3–17 show various devices inserted into the vagina.

FIG. 3A is a cross-sectional representation of a portion of the female reproductive organs, including the uterus 2 and the vagina 8 in the upright orientation.

FIG. 3B is a cross-sectional side view representation thereof. The systemic circulation 2 is a muscular organ enclosing the womb 4, and opening at the cervix 5 via the cervical canal or cervical os 6. The vagina 8 is defined by a muscular tube 10 leading from the labia minora 12 and labia majora 14 to the cervix 5.

FIG. 4A is a cross-sectional representation of FIG. 3A showing placement of a drug delivery system 16 in the vagina 8 which drugs are introduced intravaginally to the vaginal wall 10 or transmucosally to the systemic circulation 2 by way of the vaginal blood vascular and lymphatic systems. FIG. 4B is a cross-sectional representation of the vaginal area, adjacent the cervix 5, with a first embodiment of a tampon drug delivery system according to the invention. The tampon device 22 comprises an absorbent cylindrical tampon 24 comprised of fibrous material, for example cotton, having around its distal end 26 an annular delivery composition 28. The tampon device 22 places the annular delivery composition 28, supported around the distal end 26 of the tampon device 22, against the upper mucosa 18 of the vagina 8 and posterior fornix 20 for delivery through the vaginal surfaces in which the annular composition 28 is in contact. The annular composition 28 can be an annular suppository, foam, paste, gel, or any other formulation as described above, composed of suitable delivery components. The uterine discharge is absorbed by the tampon 24 and is prevented from carrying away the treatment composition.

FIGS. 5–12 depict various embodiments of devices of the invention which can be used to deliver a chemotherapeutic agent and/or inhibitor of membrane efflux systems for treatment of reproductive organ cancers according to the invention.

The device is incorporated with a mucosal composition of the invention. Numerous methods exist by which a drug can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon or other device, for example, by dissolving the drug in a pharmaceutically acceptable carrier and absorbing the drug solution into the tampon fibers. The drug can also be dissolved in a coating material which is applied to the tip of the tampon. This arrangement permits simultaneous drug delivery from the upper part of the device and absorption of the discharge or menstrual blood in the lower porous part of the tampon or tampon-like device. Alternatively, the drug can be incorporated into an insertable suppository, tablet, capsule, etc., which is placed in association with the tip of the tampon.

The tampon-like device can be constructed so as to improve drug delivery. For example, the tampon can be shaped to fit in the area of the posterior fornix and pubic symphysis and constructed so as to open up to have maximum surface area of contact for drug delivery. If the drug is in a reservoir on the surface of the device, the shape of the device should be such that it can maintain the reservoir towards a vaginal mucosal orientation for best predictable drug release characteristics.

The tampon device can also be constructed so as to have a variable absorption profile. For example, the drug area at the tip of the tampon device could be different from that of the more proximal area in order to force the drug to diffuse out into tissue, as opposed to down into the absorbent part of the tampon. Alternatively, there could be a non-absorbing channel around the cervix for the first centimeter or so in order to minimize menstrual flow from washing away the drug composition.

The release of drug from the tampon device should be timed to provide proper systemic concentration of the drug over a typical length of use of a tampon device, usually 1–8 hours.

FIG. 5 is a cross-sectional representation of the vaginal area adjacent the cervix 5 with a second embodiment of a tampon drug delivery system according to the invention. In this embodiment, tampon device 32 includes a non-porous tube 34 which communicates with the cervical os 6 for delivery of the menstrual discharge from the cervical os to an absorbent cylindrical tampon 36 comprised of fibers, for example cotton, for absorbing the discharge. The tube 34 prevents contact of the discharge with an annular drug delivery composition 38.

FIG. 6 is a cross-sectional representation of the vaginal area adjacent the cervix 5 with a third embodiment of a tampon drug delivery system according to the invention. In FIG. 6, the tampon device 42 includes a distal porous foam section 43 which is in the shape of a cup in the expanded state. In the center of the porous foam section 43 is a non-porous tube 44 which will conduct blood flow to absorbent tampon 45 proximal to the porous foam section 43. The porous foam is preferably a soft, light weight, physiologically inert foam material of polyurethane, polyester, polyether, such as described in U.S. Pat. No. 4,309,997, or other material such as collagen as described in U.S. Pat. No. 5,201,326, both incorporated herein by reference. The axial tube is preferably a non-absorptive physiologically inert material, such as rubber or plastic, and can be coated on its inner surface with an anticoagulant. The proximal end 46 of the tube 44 has a plastic loop 47 to which a string 48 may be tied for removal of the tampon device 42. The cup-shaped porous foam section 43 fits around the cervix 5 of the systemic circulation 2 and contains antineoplastic drug which may be delivered to the cervical tissue.

FIG. 7 is a cross-sectional representation of the vaginal area adjacent the cervix 5 with a fourth embodiment of a tampon drug delivery system according to the invention. In FIG. 7, the tampon device 52 includes a distal porous foam cup 54 and a proximal absorbent tampon 56. The porous foam cup 54 has a rim 58 which encircles the cervix 5, and which contains high concentrations of chemotherapeutic agent and/or inhibitor of membrane efflux systems. The rim 58 area of the porous foam cup 54 is away from the direct flow of blood. The tampon device 52 includes a string 59 for removal of the tampon device 52. FIG. 7A is a cross-sectional view of the embodiment shown in FIG. 7, taken in the direction indicated by the arrows labeled 7A in FIG. 7. As illustrated in FIG. 7A, the rim 58 area forms a ring which contains a high concentration of medication. Alternatively, as illustrated in FIG. 8, the entire porous foam cup 55 may contain medication, not just in the ringed tip area 59 near the cervix 5.

FIG. 9 is a cross-sectional representation of the vaginal area adjacent the cervix 5 with a fifth embodiment of a tampon drug delivery system according to the invention. In FIG. 9, the tampon device 62 includes a proximal absorbent tampon 64 and a distal section 66 which includes a dissolvable suppository or gel capsule 67 filled with liquid medication. The device, prior to the medication dissolution or release has a "doughnut" shape to allow for blood to pass through the center of the tampon 64. The tampon device 62 includes a string 68 attached to the tampon 64 for removal of the tampon device 62. FIG. 9A is a cross-sectional view of the of the embodiment shown in FIG. 9, taken in the direction indicated by the arrows labeled 9A in FIG. 9, and illustrates the doughnut shape of the medication filled suppository or gel capsule 67.

FIG. 10 is a cross-sectional representation of the vaginal area adjacent the cervix 5 with a sixth embodiment of a tampon drug delivery system according to the invention. In FIG. 10, the tampon device 72 includes a porous foam distal section 74 which is in the shape of a cup with "fingers" 76 which extend into the fornix areas 20 around the cervix 5. The tips of the fingers 76 contain high concentrations of medication which may be delivered to areas away from the direct flow of blood or discharge as the blood or discharge moves into absorbent tampon 78 proximal to the cup-shaped porous foam distal section 74. The tampon device 72 includes a string 79 for removal of the tampon device 72. FIG. 10A is a side view of the porous foam cup 74 and illustrates the fingers 76 which extend into the fornix areas 20 around the cervix 5 (FIG. 10).

It will be readily apparent to a person skilled in the art that the characterization of the drug delivery device as having an annular shape is only an approximate description of the shape formed by fluid or semisolid drug delivery devices positioned around a cylinder and in contact with adjacent vaginal wall mucosa, and all shapes which conform to the vaginal mucosa and external cervical surfaces are intended to be included within and indicated by the term "annular". Moreover, use of the term "annular" does not restrict the invention to the use of such devices which encircle the entire cervix (i.e. 360°). Devices which span an angle of less than 360°, but which make sufficient contact with the vaginal mucosa to deliver sufficient quantity of the drug are within the scope of the invention.

The annular drug delivery composition (FIG. 4 or 5) can be an absorbent material which expands in the presence of fluid or body heat to completely fill the space between the tampon 22, 32 and the vaginal mucosa 18.

FIG. 11 illustrates such a drug delivery device having an annular shape which does not completely encircle the entire cervix. FIG. 11 is the representation of FIG. 2 showing placement of a seventh embodiment of a tampon device 80 incorporating a scoop-shaped porous foam section 85. FIG.

12 is a side view of the tampon device 80 and FIG. 13 is a front view of the tampon device 80. The scoop-shaped porous foam section 85 is annular in shape, but does not completely encircle the cervix 5. Instead, the scoop-shaped porous foam section has a nib-shaped tip 81 which is designed to wedge itself into the posterior fornix 20. The scoop-shaped porous foam section 85 is designed to deliver medication to the vaginal wall along the entire length of the scoop-shaped porous foam section 85.

FIG. 14 is a cross-sectional representation of the vaginal area adjacent the cervix 5 with an eighth embodiment of a tampon drug delivery system according to the invention. In FIG. 14, the tampon device 82 comprises an absorbent tampon 84. The section 86 of the tampon 84 which rests against the cervix 5 contains high concentrations of medication. As the fibers absorb fluid, the tampon 84 expands around the cervix 5 and delivers medication to the tissue. The blood will be drawn to proximal sections of the tampon 84 as fibers become more absorbent in this area. The tampon device 82 includes a string 88 for removal of the tampon device 82.

Suitable cylindrical cartridge containers or inserter tubes which assist in the insertion and storage of the tampon systems of the present invention will be apparent to those skilled in the art of tampon construction. Examples are described in U.S. Pat. Nos. 4,3178,447; 3,884,233; and 3,902,493, incorporated herein by reference.

In general practice, a drug delivery device as described herein is placed into the vagina and the inserter tube is removed. The device, such as a tampon, contacts the inner wall of the vagina where the mucoadhesive agents facilitate adhesion of the drug released from the device to the vaginal wall where it is therapeutically effective.

Figure 15:
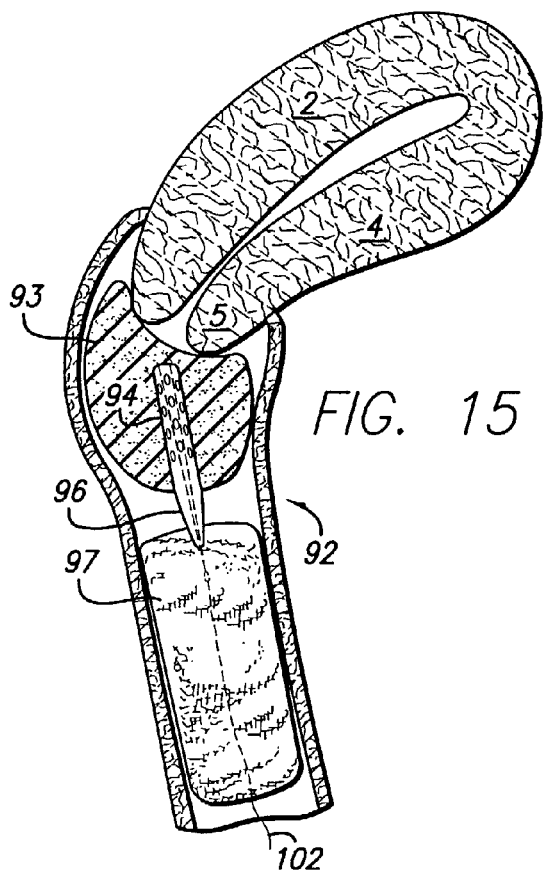
FIG. 15 is the representation of FIG. 3B showing placement of a tampon-like device incorporating non-absorbent tubing having a distal opening.
Figure 16:
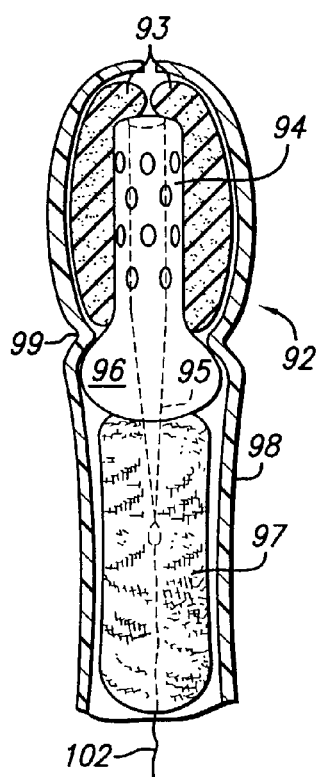
FIG. 16 is the tampon drug delivery system of FIG. 15 in a dehydrated and sheathed state.
Figure 17:
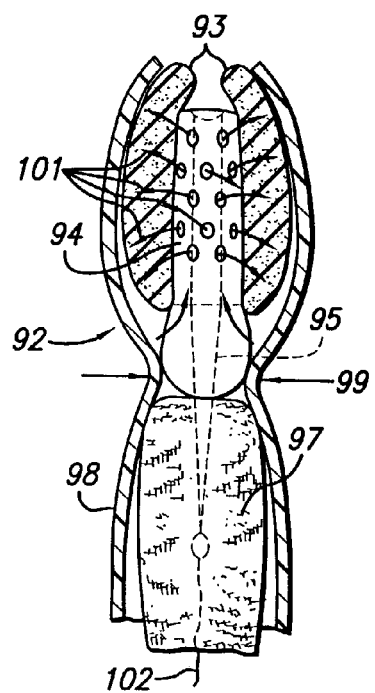
FIG. 17 is the tampon drug delivery system of FIG. 16 showing deployment of the tampon.

FIG. 15 is a cross-sectional representation of the vaginal area adjacent the cervix 5 with another embodiment of a tampon drug delivery system according to the invention. In FIG. 15, the tampon device 92 includes a distal porous foam section 93 which, in its dehydrated, sheathed state (FIG. 16), is tight around a perforated outer tube 94. The perforated outer tube 94 is connected to a bladder 96 located proximally which is filled, for example, with liquid medication. Within the perforated outer tube 94 is a concentric inner tube 95 which provides a pathway for blood to flow into an absorbent tampon 97 which is proximal to the porous foam section 93. Prior to insertion, the tampon device 92 is enveloped in a sheath 98 which is necked down at site 99 between the porous foam section 93 and the bladder 96 so that, when the tampon device 92 is deployed and the sheath 98 moves over the bladder 96, the medication is forced out seen as 101, through the perforated outer tube 94 into the porous foam section 93 (FIG. 17). The tampon device 92 includes a string 102 for removal of the tampon device 92.

Another example of a suitable controlled release drug delivery system for the present invention is the vaginal ring. Vaginal rings usually consist of an inert elastomer ring coated by another layer of elastomer containing the drug to be delivered. The rings can be easily inserted, left in place for the desired period of time, up to 7 days, then removed by the user. The ring may be solid or hollow containing the chemotherapeutic drug and/or inhibitor of membrane efflux systems or it may be a porous material releasing the drug therefrom. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

Pessaries, cups, strips, tablets and suppositories are other examples of drug delivery systems which can be used in the present invention. These systems have been used for delivery of vaginal contraceptives, and have been described extensively in the literature.

Another example of a delivery system is the vaginal sponge and foams. The desired pharmaceutical agent can be incorporated into a silicone matrix which is coated onto a cylindrical drug-free polyurethane vaginal sponge, as described in the literature.

In practice, the drug delivery systems that is a composition or a device of the invention are applied upon diagnosis of cancer. Typically, the treatment is continued for as long as needed to treat the cancer, to maintain remission state or prevent further growth.

EXAMPLE 1

Preparation of Drug Containing Vaginal Tampon-like Device for Treatment of Cancer This example describes a process for preparation of a formulation as a suppository for transvaginal delivery of doxorubicin.

Doxorubicin hydrochloride was obtained from Meiji Seika Kaisha, LTD, Japan. Vaginal suppositories were formulated and prepared 24 hours prior to administration. The three basic ingredients for the doxorubicin formulation were the lipophilic carrier SUPPOCIRE CS2 obtained from Gattefossé, Westwood, N.J. (75% wt); a mucoadhesive hydroxypropyl methylcellulose (e.g., METHOCEL K, HPMC K15M obtained from Dow Chemical, Midland, Mich. (8%/wt); and a permeation enhancing polyoxyethylene alkyl ether (e.g., TRANSCUTOL® obtained from Gattefossé (17%/wt). These ingredients were mixed in percent amounts as shown. To make eight suppositories, 4.5 grams of SUPPOCIRE CS2, 480 mg of HPMC, 1020 mg of TRANSCUTOL, and the calculated dose of drug (5 mg doxorubicin base equivalent/suppository) were weighed out.

The lipophilic carrier was melted in a 100 mL glass beaker maintained in a water bath at 65° C. until the carrier was completely liquified. The weighed amount of TRANSCUTOL was quantitatively transferred to a preweighed small mortar and pestle. The drug was added and homogeneously distributed to the Transcutol by stirring with the pestle. Then HPMC was added under continuous stirring until a homogeneous suspension was obtained which then was added to the melt under stirring.

The mixture was quickly poured into TYGON tubing molds (available from Fisher Scientific, Pittsburgh, Pa., 2×0.5 cm dimensions), followed by cooling in the upright position on an ice-cold glass slab.

Suppositories were kept refrigerated until administration. The suppository was weighed prior to each experiment to determine the actual drug dose.

The prepared suppository was then used directly or incorporated into a tampon-like vaginal device according to the invention in such a way that the drug was released from the surface of the device in a sustained time-release manner.

In an alternative arrangement, the tampon-like vaginal device was soaked with the formulation containing doxorubicin hydrochloride, dried and protected by a cardboard applicator until used.

EXAMPLE 2

Preparation of Vaginal Tampon-Like Device for Inhibitors

This example describes a process for preparation of a tampon-like device for transvaginal delivery of verapamil, an inhibitor of the membrane efflux system P-glycoprotein.

Verapamil hydrochloride obtained from Sigma-Aldrich, St. Louis, Mo. was mixed with radioactively labeled [$^3$H] verapamil (5–8 $\mu$Ci). Vaginal suppositories were formulated and prepared 24 hours prior to administration. The three basic ingredients for the verapamil formulation were the lipophilic carrier SUPPOCIRE AS2 obtained from Gattefosse, Westwood, N.J. (80%/wt); a mucoadhesive hydroxypropyl methylcellulose (e.g., METHOCEL K, HPMC K15M obtained from Dow Chemical, Midland, Mich. (10%/wt); and a permeation enhancing polyoxyethylene alkyl ether (e.g. TRANSCUTOL obtained from Gattefossé (10%/wt). These ingredients were mixed in percent amounts as shown. To make eight suppositories, 4.8 grams of SUPPOCIRE AS2, 600 mg of HPMC, 600 mg of TRANSCUTOL, and the calculated dose of drug (0.75 mg verapamil base equivalent/suppository) were weighed out. The lipophilic carrier was melted in a 100 mL disposable polypropylene beaker in a water bath at 50° C. until the carrier was completely liquefied. The weighed amount of TRANSCUTOL was quantitatively transferred to a small, pre-weighed mortar and pestle. Both hot and cold VERAPAMIL were added under stirring until a clear liquid was obtained, to which HPMC was added. Stirring was continued until a homogenous suspension was obtained. The mixture was quickly poured into TYGON tubing molds (available from Fisher Scientific, Pittsburgh, Pa., 2×0.5 cm dimensions), followed by cooling in the upright position on an ice-cold glass slab.

Suppositories were kept refrigerated until administration. The suppository was weighed prior to each experiment to determine the actual drug dose.

The prepared suppository was then used directly or incorporated into a vaginal device according to the invention in such a way that the drug was released from the surface of the device in a sustained time-release manner.

In an alternative arrangement, the tampon-like vaginal device was soaked with a formulation containing verapamil hydrochloride, dried and protected by a cardboard applicator until used.

What is claimed is:

1. A method for a transmucosal delivery of chemotherapeutic agents and inhibitors of membrane efflux systems to a systemic circulation for treatment, control and maintenance of cancer in a human female patient, wherein said agents and inhibitors are delivered into the systemic circulation transmucosally through a vaginal mucosa from a mucoadhesive composition or from an intravaginal device incorporated with said composition, said method comprising steps of:

a) providing the transmucosal vaginal composition consisting essentially of from about 0.001 to about 3000 mg of a chemotherapeutic agent selected from the group consisting of daunorubicin, doxorubicin, idarubicin, amrubicin, pirarubicin, epirubicin, mitoxantrone, etoposide, teniposide, vinblastine, vincristine, mitomycin C, paclitaxel, docetaxel, actinomycin D, colchicine, topotecan, irinotecan and gemcitabine or an inhibitor of a membrane efflux system selected from the group consisting of cyclosporin, verapamil, valspodor, biricodar, quinidine, terfenadine, pervilleine A, GF120918, LY335979, OC144-093, XR9576, probenecid, MK571 and a mixture thereof;

from about 30 to about 95% of a lipophilic or hydrophilic carrier selected from the group consisting of saturated mono-, di- or triglyceride of fatty acids from 8 to 18 carbons, a mixture thereof, polyethylene glycol of molecular weight between about 200 and 8000, a derivative thereof and a mixture thereof; from about 5 to about 25% of a mucoadhesive agent selected from the group consisting of a cellulose derivative, natural gum, alginate and pectin; and from about 5 to about 25% of a sorption promoter selected form the group consisting of a non-ionizable glycol ester derivative, a non-ionizable glycol ether derivative and an interesterified stone oil;

wherein said composition is formulated as, or incorporated into the device as, a suppository, cream, gel, foam, ointment, microparticles, microcapsules, nanoparticles or a capsule containing microparticles, microcapsules or nanoparticles, or a liposome suspension; and b) delivering said composition to the vaginal mucosa by administering said composition into the vagina or inserting said device incorporated with said composition into the vagina wherein said vaginal device is a vaginal tampon, vaginal ring, vaginal strip, vaginal capsule, vaginal tablet, vaginal pessary, vaginal cup or vaginal sponge.

2. The method of claim 1 wherein said non-ionizable glycol ester derivative is polyethylene glycol caprylic glyceride, polyethylene glycol capric glyceride, or a mixture thereof, or propylene glycol oleic glyceride, and wherein said non-ionizable glycol ether derivative is ethoxydiglycol.

3. The method of claim 2 wherein said cellulose derivative is hydroxypropyl methylcellulose.

4. The method of claim 3 wherein said lipophilic carrier is the saturated mono-, di- or triglyceride of fatty acids of from 8 to 18 carbons, or the mixture thereof and wherein said hydrophilic carrier is a polyethylene glycol (PEG) 8000, PEG 6000, PEG 4000, PEG 3000, PEG 2000, PEG 1500, PEG 400 or a mixture thereof.

5. The method of claim 4 wherein said composition comprises from about 1 to about 1000 mg of the chemotherapeutic agent or the inhibitor of the membrane efflux system, about 10% of hydroxypropyl methylceilulose, about 75% of saturated triglyceride of fatty acids for a hydrophilic drug or PEG 6000/PEG 400 for a lipophilic drug and about 15% of ethoxydiglycol.

6. The method of claim 5 wherein said chemotherapeutic agent or inhibitor of the membrane efflux system is present in from about 100 to about 1000 mg and is released from said composition or from the device incorporated with said composition in a controlled release manner for a continuous or pulsed release.

7. A mucoadhesive vaginal composition for transmucosal delivery of chemotherapeutic agents and inhibitors of membrane efflux systems to a systemic circulation for treatment, control and maintenance of cancer in a human female patient, said composition essentially consisting of:

a) from about 0.001 to about 3000 mg of the chemotherapeutic agent selected from the group consisting of daunorubicin, doxorubicin, idarubicin, amrubicin, pirarubicin, epirubicin, mitoxantrone, etoposide, teniposide, vinblastine, vincristine, mitomycin C, paclitaxel, docetaxel, actinomycin D, colchicine, topotecan, irinotecan and gemcitabine or the inhibitor of a membrane efflux system selected from the group consisting of cyclosporin, verapamil, valspodor, biricodar, quinidine, terfenadine, pervilleine A, GF120918, LY335979, OC144-093, XR9576, probenecid, MK571 and a mixture thereof;

from about 30 to about 95% of a lipophilic or hydrophilic carrier selected from the group consisting of saturated mono-, di- or triglyceride of fatty acids from 8 to 18 carbons, a mixture thereof, polyethylene glycol of molecular weight between about 200 and 8000, a derivative thereof and a mixture thereof;

from about 5 to about 25% of a mucoadhesive agent selected from the group consisting of a cellulose derivative, natural gum, alginate and pectin; and from about 5 to about 25% of a sorption promoter selected from the group consisting of a non-ionizable glycol ester derivative, a non-ionizable glycol ether derivative and an interesterified stone oil;

wherein said composition is formulated as a suppository, cream, gel, foam, ointment, microparticles, microcapsules, nanoparticles, capsule containing microparticles, microcapsules or nanoparticles, or a liposome suspension.

8. The composition of claim 7 wherein said non-ionizable alycol ester derivative is polyethylene glycol caprylic glyceride, polyethylene glycol capric glyceride, or a mixture thereof, or propylene glycol oleic glyceride and wherein said non-ionizable glycol ether derivative is ethoxydiglycol.

9. The composition of claim 8 wherein said sorption promoter is ethoxydiglycol present in from about 10 to about 15%.

10. The composition of claim 9 wherein said cellulose derivative is hydroxypropyl methylcellulose present in from about 10 to about 15%.

11. The composition of claim 10 wherein said lipophilic carrier is the saturated mono-, di- or triglyceride of fatty acids of from 8 to 18 carbons or the mixture thereof, and wherein said hydrophilic carrier is a polyethylene glycol (PEG) 8000, PEG 6000, PEG 4000, PEG 3000, PEG 2000, PEG 1500, PEG 400 or a mixture thereof.

12. The composition of claim 11 wherein said carrier for a lipophilic drug is the hydrophilic carrier selected from the group consisting of polyethylene glycol (PEG) 8000, PEG 6000, PEG 4000, PEG 3000, PEG 2000, PEG 1500, PEG 400 or a mixture thereof.

13. The composition of claim 12 wherein said carrier for a hydrophilic drug is the lipophilic carrier selected from the group consisting of the saturated mono-, di- or triglyceride of fatty acids of from 8 to 18 carbons and the mixture thereof.

14. The composition of claim 13 wherein said composition comprises from about 1 to about 1000 mg of the chemotherapeutic agent or the inhibitor of the membrane efflux system, about 10% of hydroxypropyl methylcellulose, about 75% of saturated triglyceride of fatty acids for a hydrophilic drug or a PEG 6000/PEG 400 for a lipophilic drug, and about 15% of ethoxydiglycol.

15. The composition of claim 14 wherein said chemotherapeutic agent or inhibitor of the membrane efflux system is present in from about 100 to about 1000 mg and is released from said composition or from the device incorporated with said composition in a controlled release manner for a continuous or pulsed release.

16. The composition of claim 15 additionally comprising a penetration enhancer or a solubilizer.

17. The composition of claim 16 administered daily, bi-daily, weekly, monthly or quarterly.

18. The composition of claim 17 administered once or twice daily.

19. The composition of claim 15 incorporated into an intravaginal device.

20. The composition of claim 19 incorporated into the intravaginal device wherein said device is a vaginal tampon, vaginal ring, vaginal strip, vaginal capsule, vaginal tablet, vaginal pessary, vaginal cup or vaginal sponge.

21. A medicated intravaginal device for transmucosal delivery of chemotherapeutic agents or inhibitors of a membrane efflux system to the general circulation, wherein said device is a vaginal tampon, vaginal ring, vaginal strip, vaginal capsule, vaginal tablet, vaginal bioadhesive tablet, vaginal pessary, vaginal cup or vaginal sponge incorporated with a transmucosal composition comprising from about 0.001 to about 3000 mg of the chemotherapeutic agent selected form the group consisting of daunorubicin, doxorubicin, idarubicin, amrubicin, pirarubicin, epirubicin, mitoxantrone, etoposide, teniposide, vinbiastine, vincristine, mitomycin C, paclitaxel, docetaxel, actinomycin D, colchicine, topotecan, irinotecan and gemcitabine or the inhibitor of a membrane efflux system selected from the group consisting of cyclosporin, verapamil, valspodor, biricodar, quinidine, terfenadine, pervilleine A, GF120918, LY335979, OC144-093, XR9576, probenecid, MK571 and a mixture thereof;

from about 30 to about 95% of a lipophilic or hydrophilic carrier selected from the group consisting of saturated mono-, di- or triglyceride of fatty acids from 8 to 18 carbons, a mixture thereof, polyethylene glycol of molecular weight between about 200 and 8000, a derivative thereof and a mixture thereof; from about 5 to about 25% of a mucoadhesive agent selected from the group consisting of a cellulose derivative, natural gum, alginate and pectin; and from about 5 to about 25% of a sorption promoter selected form the group consisting of a non-ionizable glycol ester derivative, a non-ionizable glycol ether derivative and an interesterified stone oil;

wherein said composition is formulated as a suppository, cream, gel, foam, ointment, microparticles, microcapsules, nanoparticles, capsule containing microparticles, microcapsules, or nanoparticles, or a liposome suspension; and wherein said composition is incorporated into said device.

22. The device of claim 21 wherein said device is incorporated with the composition comprising from about 1 to about 1000 mg of the chemotherapeutic agent or the inhibitor of the membrane efflux system, about 10% of hydroxypropyl methylcellulose, about 75% of saturated triglyceride of fatty acids for a hydrophilic drug or PEG 6000/PEG 400 for a lipophilic drug and about 15% of ethoxydiglycol.

23. The device of claim 22 wherein said device is incorporated with the composition comprising from about 100 to about 1000 mg of the chemotherapeutic agent or the inhibitor of the membrane efflux system released from said composition incorporated into said device in a controlled release manner for a continuous or pulsed release.

24. The device of claim 23 wherein said device is the vaginal tampon.

25. The device of claim 23 wherein said device is the vaginal strip.

26. The device of claim 23 wherein said device is the vaginal pessary.

27. The device of claim 23 wherein said device is the vaginal sponge.

28. The device of claim 23 wherein said device is the vaginal foam.

29. The device of claim 23 wherein said device is the vaginal ring.

30. The device of claim 23 wherein said device is the vaginal capsule.

31. The device of claim 23 wherein said device is the vaginal tablet.

32. The device of claim 23 wherein said device is the vaginal bioadhesive tablet.

33. The device of claim 23 wherein said device is the vaginal cup.

* * * * *